US011125083B2

(12) United States Patent
Jones et al.

(10) Patent No.: US 11,125,083 B2
(45) Date of Patent: Sep. 21, 2021

(54) FOCUSED FORMATION SAMPLING METHOD AND APPARATUS

(71) Applicant: Halliburton Energy Services, Inc., Houston, TX (US)

(72) Inventors: Christopher Michael Jones, Katy, TX (US); Darren George Gascooke, Houston, TX (US); Anthony Herman Van Zuilekom, Houston, TX (US); Marcelo Civarolo, The Woodlands, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 106 days.

(21) Appl. No.: 16/670,886

(22) Filed: Oct. 31, 2019

(65) Prior Publication Data

US 2021/0131283 A1  May 6, 2021

(51) Int. Cl.
*E21B 49/10* (2006.01)
*G01N 33/24* (2006.01)
*E21B 33/124* (2006.01)

(52) U.S. Cl.
CPC ............ *E21B 49/10* (2013.01); *E21B 33/124* (2013.01); *G01N 33/241* (2013.01)

(58) Field of Classification Search
CPC ........ E21B 49/10; E21B 49/08; E21B 49/082; E21B 49/081
See application file for complete search history.

(56) References Cited

U.S. PATENT DOCUMENTS

| | | |
|---|---|---|
| 6,301,959 B1 | 10/2001 | Hrametz |
| 8,210,260 B2 | 7/2012 | Milkovisch et al. |
| 8,967,242 B2 | 3/2015 | Evans, II et al. |
| 9,057,250 B2 | 6/2015 | Zazovsky et al. |
| 9,163,500 B2 | 10/2015 | Tao et al. |
| 9,303,509 B2 | 4/2016 | Milkovisch et al. |
| 9,534,987 B2 | 1/2017 | Yushko et al. |
| 9,557,312 B2 | 1/2017 | Zuo et al. |

(Continued)

OTHER PUBLICATIONS

Foreign Communication from Related Application—International Search Report and Written Opinion of the International Searching Authority, International Application PCT/US 2019/061987, dated Jul. 27, 2020, 11 pages.

*Primary Examiner* — Kipp C Wallace
(74) *Attorney, Agent, or Firm* — Conley Rose, P.C.; Rodney B. Carroll

(57) ABSTRACT

A focused sampling method comprising: allocating fluid flow from a guard zone through a guard line and from a sample zone through a sample line, the guard zone being positioned at least partially concentrically about the sample zone and the guard zone, and the sample zone being in fluid communication with a formation; pumping, via a common line, a combined fluid flow from the formation through to a discard line for a pre-sampling time period, the combined flow comprising the fluid flow allocated from the guard zone into the guard line and the fluid flow allocated from the sample zone into the sample line; subsequent the pre-sampling time period, discontinuing flow from the guard line into the common line, such that the combined flow comprises only the fluid flow from the sample line; and introducing the combined flow comprising the fluid flow from the sample line into a sample chamber.

20 Claims, 9 Drawing Sheets

(56) References Cited

U.S. PATENT DOCUMENTS

| | | |
|---|---|---|
| 10,101,484 B2 | 10/2018 | Pomerantz et al. |
| 10,125,596 B2 | 11/2018 | Waid et al. |
| 10,184,334 B2 | 1/2019 | Betancourt-Pocaterra et al. |
| 2004/0000433 A1 | 1/2004 | Hill et al. |
| 2008/0073078 A1* | 3/2008 | Sherwood ............... E21B 49/10 166/264 |
| 2010/0050760 A1* | 3/2010 | Vannuffelen ....... G01N 21/1717 73/152.27 |
| 2010/0175873 A1* | 7/2010 | Milkovisch .............. G01N 1/24 166/264 |
| 2012/0053838 A1* | 3/2012 | Andrews ............... E21B 49/082 702/8 |
| 2013/0019671 A1 | 1/2013 | Stibbe et al. |
| 2013/0276553 A1 | 10/2013 | Yushko et al. |
| 2013/0293891 A1* | 11/2013 | Zazovsky ............ G01J 3/0267 356/402 |
| 2015/0361791 A1* | 12/2015 | Gisolf .................... E21B 49/08 166/264 |
| 2016/0130940 A1* | 5/2016 | Hsu ........................ E21B 49/10 702/11 |
| 2016/0168985 A1 | 6/2016 | Betancourt-Pocaterra et al. |
| 2017/0152743 A1* | 6/2017 | Gisolf .................... G01N 1/14 |
| 2018/0003049 A1* | 1/2018 | Gisolf .................... E21B 34/06 |

\* cited by examiner

# pFOCUSED FORMATION SAMPLING METHOD AND APPARATUS

TECHNICAL FIELD

The present disclosure relates generally to systems and methods for obtaining one or more samples of formation fluid having a desired purity from a wellbore penetrating a subterranean formation via a focused sampling device comprising a single pump and optionally at least one dead volume.

BACKGROUND

Wellbores are drilled to locate and produce hydrocarbons from a formation. A wellbore is formed by advancing a downhole drilling tool with a drill bit at an end thereof into the ground. As the drilling tool is advanced, a drilling mud is generally pumped through the drilling tool and out the drill bit to cool the drilling tool and carry away drill cuttings. The drilling mud with associated drill cuttings exits the drill bit and flows back up to the surface prior to recirculation through the drilling tool. The drilling mud is also utilized to create a mudcake that lines the wellbore. During and/or subsequent to the drilling operation, testing is typically performed to evaluate the formations penetrated by the wellbore. In some applications, the drilling tool is provided with one or more devices to test and/or sample fluids from the surrounding formation. In some applications, the drilling tool is removed from the wellbore and a wireline tool deployed into the wellbore in order to test and/or sample fluids from the formation. These fluid samples or tests can be utilized, for example, to locate valuable hydrocarbons.

Various challenges can be encountered in the process of obtaining uncontaminated fluid samples from subterranean formations. For example, with reference to the petroleum-related industries, the area around the borehole from which fluid samples are sought typically contains contaminants, such as filtrate from the drilling mud utilized for drilling the wellbore. Such filtrate (for example, oleaginous fluid from an oil based drilling fluid) can contaminate the formation fluid as it passes through the borehole, resulting in fluid that is generally unacceptable for hydrocarbon fluid sampling and/or evaluation. A sample of formation fluid having an undesired amount of one or more contaminants can be referred to as 'contaminated fluid'. Because fluid is typically sampled through the sidewalls of the wellbore (which may contain mudcake, cement and/or other layers), it is difficult to avoid contamination of the formation fluid as it flows from the formation and into a downhole tool during sampling. A challenge thus lies in minimizing the contamination level of the virgin formation fluid during fluid extraction from the formation.

Accordingly, there exists a need for a system and method of obtaining formation fluid samples of desired purity from a wellbore.

BRIEF SUMMARY OF THE DRAWINGS

For a more complete understanding of this disclosure, reference is now made to the following brief description, taken in connection with the accompanying drawings and detailed description, wherein like reference numerals represent like parts.

DETAILED DESCRIPTION

Figure 1:
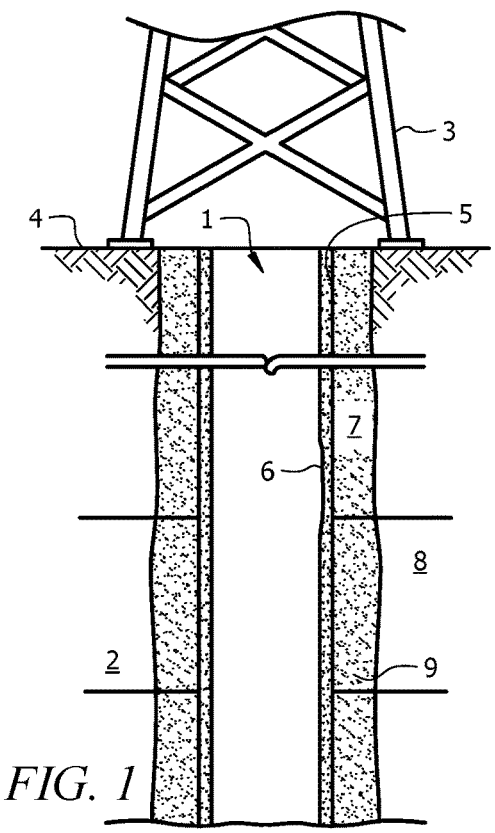
FIG. 1 is a schematic view of a subsurface formation penetrated by a wellbore lined with mudcake, depicting the clean or virgin fluid in the subsurface formation.

It should be understood at the outset that although an illustrative implementation of one or more embodiments are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents.

The terms "focused sampling" and "focused formation sampling" are utilized interchangeably herein and can refer to sampling of formation by manipulating the location of clean and contaminated formation fluid in the region of the formation in which the sampling is performed.

The terms "formation tester", "sampling device", "focused sampling device", "sampling system" and "focused sampling system" 30 (e.g., 30A-30F in FIGS. 5 and 7-11, respectively, described hereinbelow) are utilized interchangeably herein.

The term "formation" as utilized herein includes a subsurface formation, a subterranean formation, and a subsea formation.

As utilized herein, the terms 'virgin fluid', 'acceptable virgin fluid', 'uncontaminated fluid', 'virgin sample', and the like are utilized to indicate a subsurface fluid that is pure, pristine, connate, uncontaminated, unadulterated, or otherwise considered in the fluid sampling and analysis field to be sufficiently or acceptably representative (e.g., to have a purity above a desired level and/or a level of contaminants below a desired level) of a given formation for valid hydrocarbon sampling and/or evaluation. A virgin fluid can be representative of the composition of unadulterated formation fluid under ambient formation conditions. As utilized herein, therefore, the "purity" indicates a degree to which a fluid (e.g., a composition thereof) approaches the virgin fluid (e.g., a composition thereof), and "contamination" and "contaminants" relate to components of a fluid not present in the virgin formation fluid and/or present in the fluid at a level above a level thereof in the virgin formation fluid. That is, as utilized herein, a "pure" fluid comprises a composition of the virgin formation fluid.

As utilized herein, "flow rate" can refer to volumetric flow rate (e.g., cm$^3$/s).

The sampling system and method of this disclosure are herein referred to as a "focused sampling system and method", as they provide a technique to achieve an at least partially focused sample and obtain advantages of full focused sampling, but with a single pumpout system.

A descriptor numeral can be utilized generically herein to refer to any embodiment of that component. For example, a downhole tool 10 (also referred to as a sampling downhole tool, a formation tester, or sampling tool) can refer to a downhole tool 10 as depicted and described with reference to FIG. 1 and FIG. 2, a downhole tool 10' as depicted and described with reference to FIG. 3, a downhole tool 10" as depicted and described with reference to FIG. 4, a downhole tool 10A as depicted and described with reference to FIG. 5, a downhole tool 10B as depicted and described with reference to FIG. 7, a downhole tool 10C as depicted and described with reference to FIG. 8, a downhole tool 10D as depicted and described with reference to FIG. 9, a downhole tool 10E as depicted and described with reference to FIG. 10, or a downhole tool 10F as depicted and described with reference to FIG. 11. A one or more dead volume 45 can be utilized to indicate one or more dead volumes 45A and/or dead volumes 45B as depicted and described herein with reference to FIG. 5, one or more dead volumes 45C as depicted and described with reference to FIG. 9, one or more dead volumes 45D as depicted and described with reference to FIG. 10, and/or one or more dead volumes 45D as depicted and described with reference to FIG. 11. A focused sampling system 30 can refer to a focused sampling system 30A as depicted and described with reference to FIG. 5, a focused sampling system 30B as depicted and described with reference to FIG. 7, a focused sampling system 30C as depicted and described with reference to FIG. 8, a focused sampling system 30D as depicted and described with reference to FIG. 9, a focused sampling system 30E as depicted and described with reference to FIG. 10, and/or a focused sampling system 30F as depicted and described with reference to FIG. 11. A probe 40 can refer to a dual focused sampling probe 40, 40A, or 40B as depicted and described herein with reference to FIG. 1, FIG. 2, or FIG. 3, respectively, and/or a probe 40C as depicted and described herein with reference to FIG. 7.

Herein disclosed are systems and methods for formation evaluation. Formation evaluation typically requires that fluid from the formation be drawn into a downhole drilling tool and/or a wireline tool for testing and/or sampling. Various devices, such as probes, are typically extended from the downhole tool to establish fluid communication with the formation surrounding the wellbore and to draw fluid into the downhole tool. A typical probe is a circular or prolate element that extends from the downhole tool and is thus positioned against a sidewall of the wellbore. A rubber packer at the end of the probe can be used to create a seal with the sidewall of the wellbore. In applications, a dual packer can be used to form a seal with the sidewall of the wellbore. With a dual packer, two elastomeric rings expand radially above and below the downhole tool to isolate a portion of the wellbore therebetween. The rings form a seal with the sidewall of the wellbore and permit fluid to be drawn into the isolated portion of the wellbore and into one or more inlets in the downhole tool. The mudcake lining the wellbore is often useful in assisting the probe and/or dual packers in making the seal with the sidewall of the wellbore. Once the seal is made, fluid from the formation can be drawn into the downhole tool through one or more inlets by lowering the pressure in the downhole tool relative to ambient formation pressure.

The collection and sampling of underground fluids contained in subsurface formations is well known. In the petroleum exploration and recovery industries, for example, samples of formation fluids are collected and analyzed for various purposes, such as to determine the existence, composition and/or producibility of subsurface hydrocarbon fluid reservoirs. This component of the exploration and recovery process can be crucial for developing drilling strategies, and can significantly impact financial expenditures. To conduct valid fluid analysis, the fluid samples obtained from the subsurface formation should be of sufficient purity, or be virgin fluid, to adequately represent the fluid contained in the formation and thus enable an accurate formation evaluation to be based thereon.

FIG. 1 depicts a subsurface formation 2 penetrated by a wellbore 1. A layer of mudcake (or filter cake) 6 formed by circulation of a drilling fluid (or drilling mud) lines a sidewall 5 of the wellbore 1. Due to invasion of mud filtrate into the formation 2 during drilling, the wellbore 1 is surrounded by a cylindrical region known and referred to herein as an "invaded" or "dirty" or "contaminated" zone 7. Invaded zone 7 contains contaminated fluid 9 that may or may not be mixed with virgin uncontaminated formation fluid 8. Beyond the sidewall 5 of the wellbore 6 and surrounding contaminated fluid 9, virgin fluid 8 is located in the formation 2.

Figure 2:
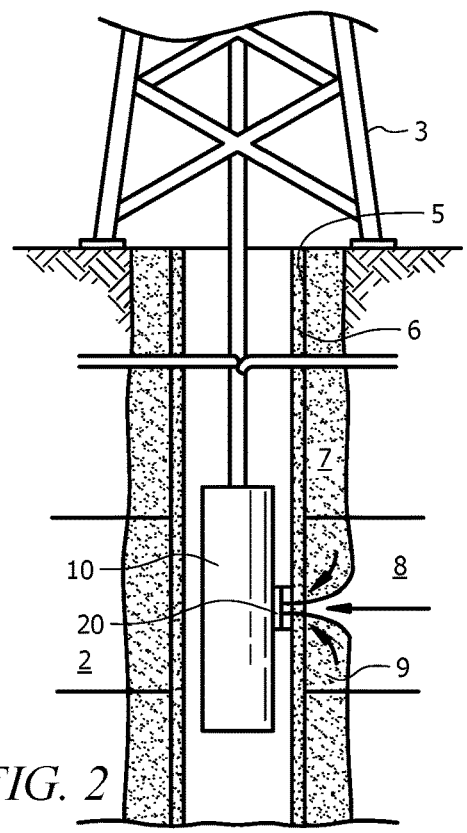
FIG. 2 is a schematic view of a downhole tool positioned in the wellbore of FIG. 1 with a component such as a probe extending to the formation, depicting a possible flow of contaminated and virgin fluid into a downhole sampling tool.

As shown in FIG. 1, contaminants (mud filtrate such as oleaginous fluids) tend to be located near the sidewall 5 of wellbore 6 in the invaded zone 7. FIG. 2 shows the typical flow patterns of the formation fluid as it passes from subsurface formation 2 into a downhole tool 10. The downhole tool 10 is positioned adjacent the formation 2 and a component 20 of the downhole tool 10 (such as a probe) is extended from the downhole tool 10 through the mudcake 6 to the sidewall 5 of the wellbore 1. The component 20 is placed in fluid communication with the formation 2 so that formation fluid may be passed into the downhole tool 10. Initially, as shown in FIG. 1, the invaded zone 7 that contains contamination surrounds the sidewall 5 in contact with component (e.g., probe) 20.

As fluid initially passes into the component 20, all or a portion of the fluid drawn into the component 20 comprises contaminated fluid 9 from the invaded zone 7, thereby providing fluid that can be unsuitable for sampling (e.g., having a purity that is below a desired purity and/or a level of contaminants above a desired level of contaminants). However, as shown in FIG. 2, after a certain amount of fluid passes through the component 20 into the downhole tool 10, the virgin formation fluid 8 breaks through and begins entering the component 20. That is, a more central portion of the fluid flowing into the component 20 gives way to the virgin fluid 8, while the remaining portion of the fluid is contaminated fluid 9 from the invaded zone 7. The challenge is to adapt the flow of the fluid into the component 20 and/or the configuration of the component 20 (e.g., probe) so that the virgin formation fluid 8 is collected in the downhole tool 10 during the fluid sampling.

As described with reference to FIG. 1 and FIG. 2, formation evaluation is typically performed on fluids drawn into the downhole tool 10. Techniques for performing various measurements, pretests and/or sample collection of fluids that enter the downhole tool 10 exist, and various methods and apparatus have been proposed for obtaining subsurface fluids for sampling and evaluation. However, when the formation fluid passes into the downhole tool 10, various contaminants, such as wellbore fluids and/or drilling mud, can enter the downhole tool 10 with the formation fluids. These contaminants can affect the quality of measurements and/or the quality of fluid samples of the formation fluids taken during the sampling process. Additionally, contamination can result in costly delays in the wellbore operations due to the need for additional time for additional testing and/or sampling. Furthermore, such problems may yield results that are inaccurate and/or unreliable for formation evaluation. Despite advances in formation fluid sampling, there remains a need to develop techniques for fluid sampling that optimize the quality of the sample(s) and/or the efficiency of the sampling process. To increase sample quality, it is desirable that the formation fluid entering into the downhole tool 10 be sufficiently uncontaminated for valid testing. The formation fluid samples should have little or no contamination.

Figure 3:
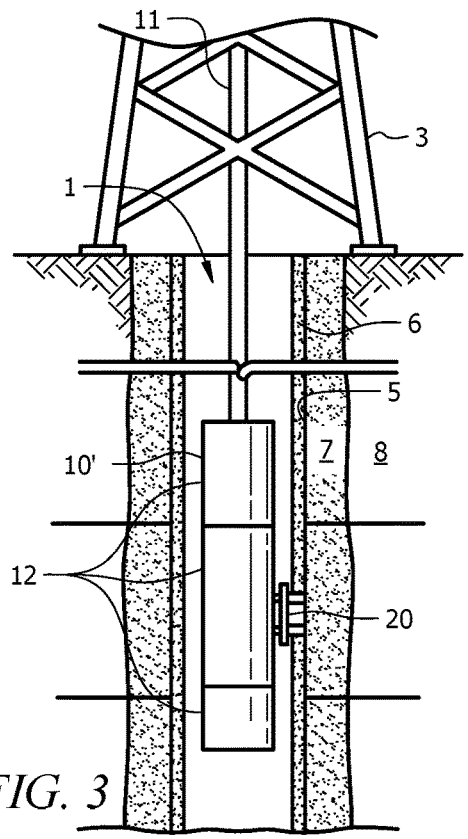
FIG. 3 is a schematic view of downhole wireline tool comprising a focused fluid sampling device, according to embodiments of this disclosure.

FIG. 3 depicts an example environment with which embodiments of the present disclosure can be employed. In the embodiment of FIG. 3, a downhole tool 10' is deployed into borehole 1 and suspended therein with a conveyance (such as conventional wireline 11, conductor or conventional tubing, or coiled tubing) below a rig 3. The illustrated downhole tool 10' is provided with various modules and/or components 12 (e.g., sampling and/or testing modules, a power module, a communication module, a pumping module, and the like), including, but not limited to, component 20 in contact with sidewall 5 of wellbore 1 and used to obtain fluid samples from the subsurface formation 2. The downhole 10' comprises a focused sampling system 30, as described hereinbelow with reference to FIG. 5 and FIGS. 7-11. The focused sampling system includes a component(s) 20 extendable through the mudcake 6 and to sidewall 5 of the wellbore 1 for collecting samples. The samples are drawn into the downhole tool 10' via the focused sampling system 30.

Figure 4:
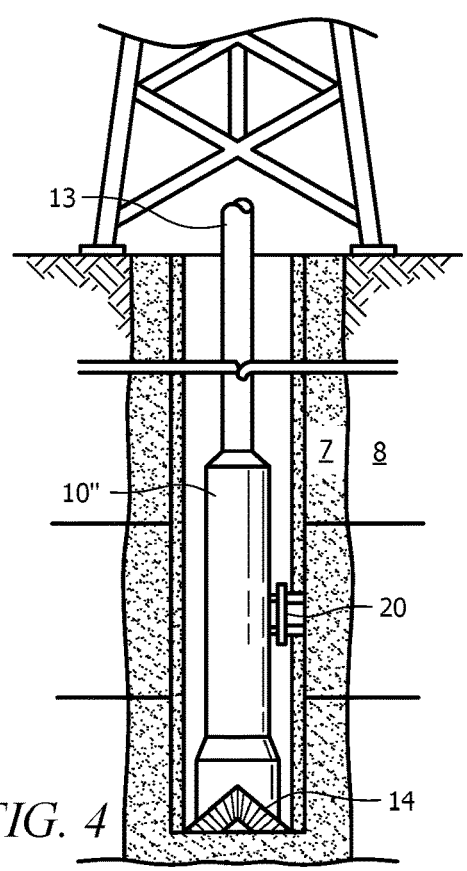
FIG. 4 is a schematic view of a downhole drilling tool comprising a focused fluid sampling device, according to embodiments of this disclosure.

While FIG. 3 depicts a modular wireline downhole tool 10' for collecting samples according to embodiments of the present disclosure, it will be appreciated by those of skill in the art a focused sampling system 30 of this disclosure can be utilized in any downhole tool 10. For example, FIG. 4 shows an alternate environment in which a downhole tool 10" comprising a focused sampling system 30 of this disclosure can be utilized while drilling a wellbore. In the embodiment of FIG. 4, the drill bit 14 and downhole tool 10" are included as part of a bottom hole assembly (BHA) coupled to a drill string 13. The downhole tool 10" may be of a variety of drilling tools, such as a Measurement-While-Drilling (MWD), Logging-While Drilling (LWD) or other drilling system. The downhole tools 10' and 10" of FIG. 3 and FIG. 4, respectively, may have alternate configurations, such as modular, unitary, wireline, coiled tubing, autonomous, drilling and other variations of downhole tools, as will be apparent to those of skill in the art upon reading this disclosure.

According to this disclosure, a downhole tool 10/10'/10" comprises a focused sampling system 30 (e.g., a focused sampling system 30A-30F, as described hereinbelow with reference to FIGS. 5 and 7-11, respectively) as described herein. As noted above, a focused sampling system of this disclosure will generically be referred to as focused sampling system "30", and can be any one of focused sampling systems 30A-30F described hereinbelow, or a focused sampling system comprising a combination of the features detailed herein, such as in focused sampling systems 30A-30F (e.g., a focused sampling system such as focused sampling system 30A of FIG. 5, focused sampling system 30B of FIG. 7 or focused sampling system 30C of FIG. 8 including one or more dead volumes 45 as described with reference to focused sampling system 30D of FIG. 9, focused sampling system 30E of FIG. 10, and/or a focused sampling system 30F of FIG. 11). The herein disclosed focused sampling systems and methods enable the flow of the fluid into the focused sampling system 30 to be adapted so that sufficiently uncontaminated formation fluid 8 (e.g., formation fluid having a purity above a desired purity and/or a level of contamination below a maximum acceptable contamination level) is collected in the downhole tool 10 during sampling.

Herein disclosed are systems and methods for obtaining one or more samples of formation fluid from a formation, such that the one or more samples have a desired purity (e.g., a contamination level below a maximum contamination level). The maximum contamination (or "threshold") level can comprise a total amount of less than or equal to 15, 14, 13, 12, 11, 10, 9, 8, 7, 6, 5, 4, 3, 2, or 1 weight percent of one or more contaminants. The one or more contaminants comprise components of a fluid that are not present in the virgin fluid and/or present in the fluid at a level greater than a level thereof in the virgin fluid.

A focused sampling system of this disclosure can comprise a sample line having a sample line inlet and a sample line outlet; a guard line having a guard line inlet and a guard line outlet; a common line having a common line inlet and a common line outlet, wherein the common line inlet is fluidly connected with the sample line outlet and the guard line outlet, and wherein the common line outlet is fluidly connected with a pump suction side inlet; the pump, wherein a discharge side outlet of the pump is fluidly connected with a discard line and a sampling line, wherein the sampling line is fluidly connected with one or more sample chambers; one or more fluid identification ID sensors positioned on the guard line, the sample line, the common line, or a combination thereof; and a flow restrictor operable to prevent flow of fluid from the guard line to the common line. These components of a focused sampling system will be detailed hereinbelow.

A focused sampling system of this disclosure will now be described with reference to FIG. 5, which is a schematic of a focused sampling system 30A comprising downhole tool 10A. Focused sampling system 30A comprises a sample line 61; a guard line 51; a common line 71; a pump 75; a discard line 72; a sampling line 81; one or more sample chambers 90 (with five, including first sample chamber 90A, second sample chamber 90B, third sample chamber 90C, fourth sample chamber 90D, and fifth sample chamber 90E depicted in the embodiment of FIG. 5); one or more fluid ID sensors S positioned on the guard line, the sample line, the common line, or a combination thereof (with first fluid ID sensor S1 and third fluid ID sensor S3 depicted on sample line 61, second fluid ID sensor S2 depicted on guard line 51, fourth fluid ID sensor S4 depicted on common line 71, and fifth fluid ID sensor S5 depicted on pump outlet line 76); and flow restrictor 55.

Sample line 61 has a sample line inlet 61A and a sample line outlet 61B. Guard line 51 has a guard line inlet 51A and a guard line outlet 51B. As depicted in the embodiment of FIG. 5, a focused sampling system 30 of this disclosure can comprise one or a plurality of lines that extend from guard line inlets 51A thereof and merge to form a single guard line 51 toward guard line outlet 51B. This configuration of guard line is intended to be included in the term "guard line(s) 51". In embodiments, the guard line(s) 51 is configured for a higher fluid flow rate $Q_G$ than a fluid flow rate $Q_S$ of the sample line 61. Common line 71 has a common line inlet 71A and a common line outlet 71B, and is fluidly connected with the sample line outlet 61B and the guard line outlet 51B, for example at a tee or Y junction. Pump 75 has a suction side inlet 75A and a discharge side outlet 75B. Suction side inlet 75A of pump 75 is fluidly connected with common line outlet 71B and discharge side outlet 75B of pump 75 is fluidly connected with discard line 72 and sampling line 81, for example via a tee or Y junction. In embodiments, focused sampling system 30 of this disclosure comprises a single pump 75, whereby fluid is pulled into the tool via a common pump (e.g., single pump 75) and a common suction line (e.g., common line 71). Sampling line 81 is fluidly connected with the one or more sample chambers 90.

Flow restrictor 55 is operable to prevent flow of fluid from guard line 51 to common line 71 in a first (e.g., closed) configuration and allow flow of fluid from the guard line 51 to the common line 71 in a second (e.g., open) configuration. In embodiments, flow restrictor 55 is a shutoff valve. In embodiments, guard line(s) 51 has a flow restrictor thereupon, such as restrictor valve $V_R$, that is operable as a shutoff valve that can be actuated to prevent fluid flow through guard line 61. In some such embodiments, a separate restrictor 55 may not be present. Flow restrictor 55 can be a check valve. Restrictor 55 can be positioned on guard line 51 upstream of guard line outlet 61B. Sample line 61 can comprise a check valve upstream of sample line outlet 51B in embodiments.

A focused sampling system 30 of this disclosure can further comprise a probe defining a sample zone fluidly connected with the sample line inlet of the sample line, a guard zone fluidly connected with the guard line inlet of the guard line, or both a sample zone fluidly connected with the sample line inlet of the sample line and a guard zone fluidly connected with the guard line inlet of the guard line. For example, focused system 30A of the embodiment of FIG. 5 further comprises probe 40 defining sample zone 60 fluidly connected with the sample line inlet 61A of the sample line 61, and guard zone 50 fluidly connected with the guard line inlets 51A of the guard line 51. The guard zone 50 and the sample zone 60 are in fluid communication with the subsurface formation 2, during operation of the focused sampling system 30.

The comparative flow rate $Q_G$ in the guard line(s) 51 from guard zone(s) 50 and flow rate $Q_S$ in the sample line 61 from sample zone 60 (see, for example, FIG. 6A and FIG. 6B) can be represented by a ratio of flow rates $Q_G/Q_S$. (The flow rate into the sample line 61 from the sample zone is represented by $Q_S$, and is also referred to herein as the flow rate in the sample zone, and the flow rate into the guard line(s) from the guard zone(s) 50 is represented by $Q_G$, and is also referred to herein as the flow rate in the guard zone(s).) The flow rate $Q_S$ in the sample line 61 from sample zone 60 may be selectively increased and/or the flow rate $Q_G$ in the guard line(s) 51 from guard zone(s) 50 may be decreased to allow more fluid to be drawn into the sample zone 60. Alternatively, the flow rate $Q_S$ in the sample line 61 from sample zone 60 may be selectively decreased and/or the flow rate $Q_G$ in the guard line(s) 51 from guard zone(s) 50 may be increased to allow less fluid to be drawn into the sample line 61 via sample zone 60. As a focused sampling system 30 of this disclosure comprises a single pump 75, a restrictor valve 55 and/or diameter of sample line 61 and/or guard line(s) 51 can be selected to provide the desired ratio $Q_G/Q_S$ of fluid flow rate in the guard zone(s) 50 to the fluid flow rate in the sample zone 60.

The flow rate may be altered to affect the flow of fluid and optimize the intake of virgin fluid into the downhole tool 10/focused sampling system 30. Various devices may be used to measure and adjust the rates to optimize the fluid flow. Initially, it may be desirable to have increased flow into the guard zone(s) 50 when the amount of contaminated fluid is high, and then adjust the flow rate to increase the flow into the sample zone 60 once the amount of virgin fluid entering the sample zone 60 increases. In this manner, the fluid sampling may be manipulated to increase the efficiency of the sampling process and the quality of the sample with which the one or more sample chambers 90 are filled and/or the quality of a sample analyzed via the one or more sensors S to evaluate formation 2.

The guard zone 50 can be positioned at least partially concentrically (e.g., concentrically) about the sample zone 60. The sample zone 60 and the guard zone 50 can be prolate (e.g., oval) or circular in cross section. For example, FIG. 6A is a schematic end view (from the perspective of wellbore wall in contact with the probe) of a focused sampling probe 40A. In FIG. 6A, focused sampling probe 40A comprises an inner concentric ring 43A and an outer concentric ring 43B, that define sample zone 60 (e.g., within inner concentric ring 43A) and guard zone 50 (e.g., between inner concentric ring 43A and outer concentric ring 43B). In FIG. 6A, inner concentric ring 43A and outer concentric ring 43B are oval in cross section shape, thus defining a guard zone 50 having an oval cross section and a sample zone 60 having an oval cross section. One or more sample zone fluid inlets 68B are fluidly connected with sample line inlet 61A of sample line 61 and one or more guard zone fluid inlets 68A are fluidly connected with guard line inlet(s) 51A of guard line 51. A sample zone fluid inlet 68B can be positioned within sample zone 60 such that a distance is maximized between sample zone fluid inlet 68B and one or more guard zone fluid inlets 68A. FIG. 6B is a schematic end view (from the perspective of wellbore wall in contact with the probe) of a focused sampling probe 40B. In FIG. 6B, inner concentric ring 43A and outer concentric ring 43B are circular (i.e., substantially round) in cross section shape, thus defining a guard zone 50 having a circular cross section and a sample zone 60 having a circular cross section. One or more sample zone fluid inlets 68B are fluidly connected with sample line inlet 61A of sample line 61 and one or more guard zone fluid inlets 68A are fluidly connected with guard line inlet(s) 51A of guard line 51. A sample zone fluid inlet 68B can be positioned at a center of sample zone 60 and one or more guard zone fluid inlets 68A are positioned about 10, 20, 30, 40, 50, 60, 70, 80, or 90% of the radial distance between inner concentric ring 43A and outer concentric ring 43B from inner concentric ring 43A. Oval focused sampling probe 40A or FIG. 6A or round focused sampling probe 40B of FIG. 6B can be utilized in the focused sampling system 30A of FIG. 5, the focused sampling system 30D of FIG. 9, the focused sampling system 30E of FIG. 10, or the focused sampling system 30F of FIG. 11. As noted above, when component 20 of the downhole tool 10 comprises a probe 40/40A/40B, once the downhole tool 10 is positioned adjacent the formation 2, the probe can be extended from the downhole tool 10 through the mudcake 6 to the sidewall 5 of the wellbore 1, such that the inlets 68 are in contact with the wellbore sidewall 5.

Figure 7:
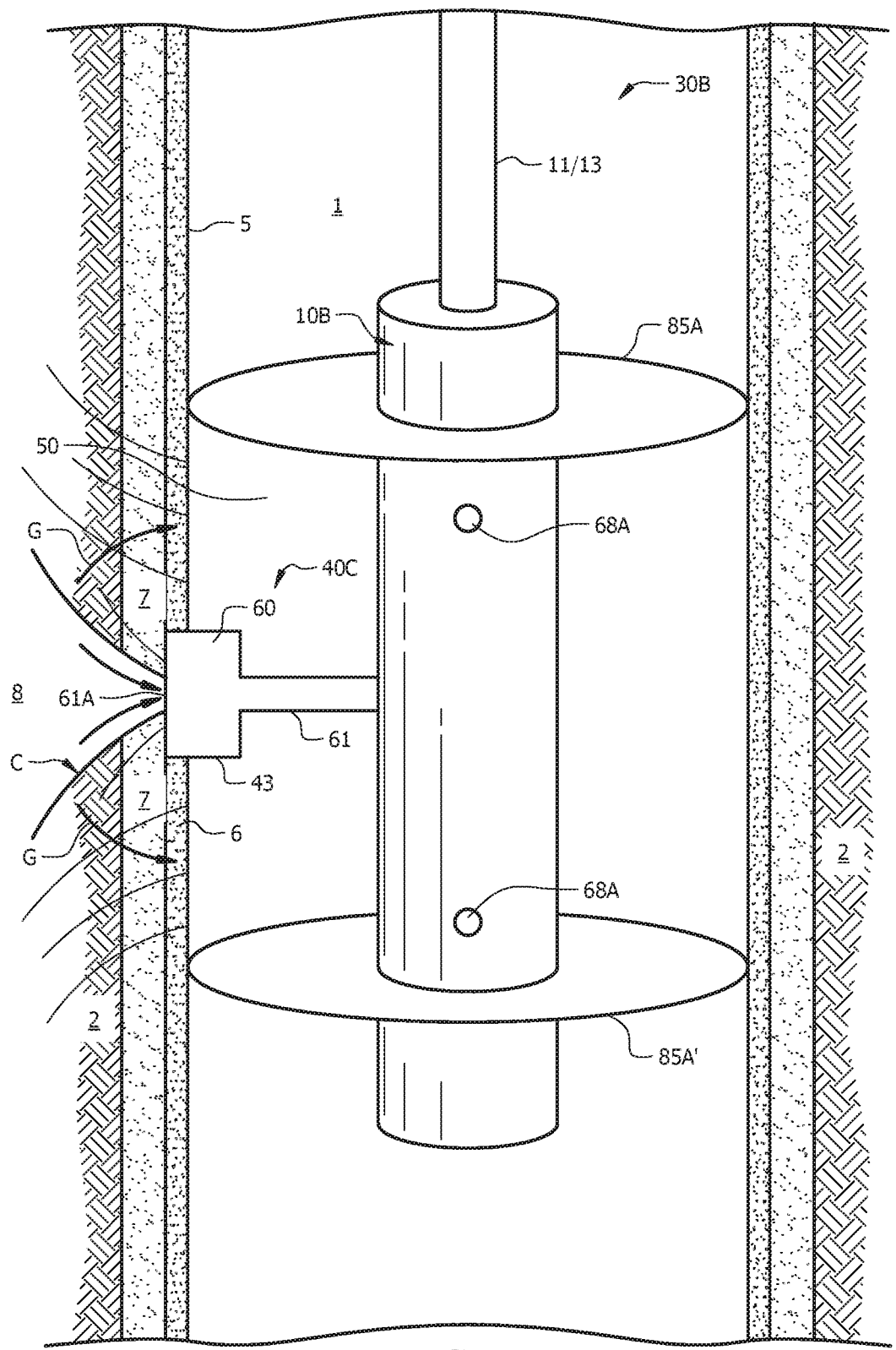
FIG. 7 is a schematic of a focused sampling system.

A focused sampling system 30 of this disclosure can comprise a combination packer/probe design, wherein the component of the focused sampling system 30 that contacts sidewall 5 of wellbore 1 include a probe and one or more packers or sets of packers. The packers of this disclosure can be any device capable of sealing the wellbore 1 to provide the sample zone 60 and/or the guard zone(s) 50, as described hereinbelow, such as elastomeric packers or any other suitable device. For example, FIG. 7 is a schematic of a focused sampling system 30B comprising downhole tool 10B. Focused sampling system 30B comprises, as component 20 (FIG. 1) that contacts sidewall 5 during operation, a probe 40C and a set of packers within wellbore 1, including upper packer 85A located within wellbore 1 above focused sampling probe 40C and lower packer 85A' located within wellbore 1 below focused sampling probe 40C. When deployed, upper packer 85A, lower packer 85A', and probe 40C extend through mudcake 6 and contact sidewall 5 of wellbore 1, thus preventing flow of fluid within wellbore 1 from above upper packer 85A or below packer 85A' from flowing past upper packer 85A or lower packer 85A', respectively. Probe 40C defines sample zone 60 and upper packer 85A and lower packer 85B define guard zone 50. In this combination packer/probe design, the probe 40C defines the sample zone 60 in fluid communication with the sample line inlet 61A of the sample line 61, while the one or more packers (e.g., a packer set comprising upper packer 85A and lower packer 85A') define the guard zone 50, wherein the guard zone 50 comprises the annulus around downhole tool 1010B (e.g., the portion of focused sampling system 30B from which probe 40C extends upon deployment) and probe 40C below upper packer 85A and above lower packer 85A', and wherein the guard zone 50 is in fluid communication with the guard line inlet 51A of the guard line 51. One or more guard zone fluid inlets 68A along the body of downhole tool 10B provide passage for fluid from guard zone 50 into guard line inlet 51A of the guard line 51. The probe 40C can comprise a ring 43 that defines sample zone 60. Although described as a ring 43, probe 40C can define a sample zone 60 having any cross sectional shape when deployed along sidewall 5 of wellbore 1.

Figure 8:
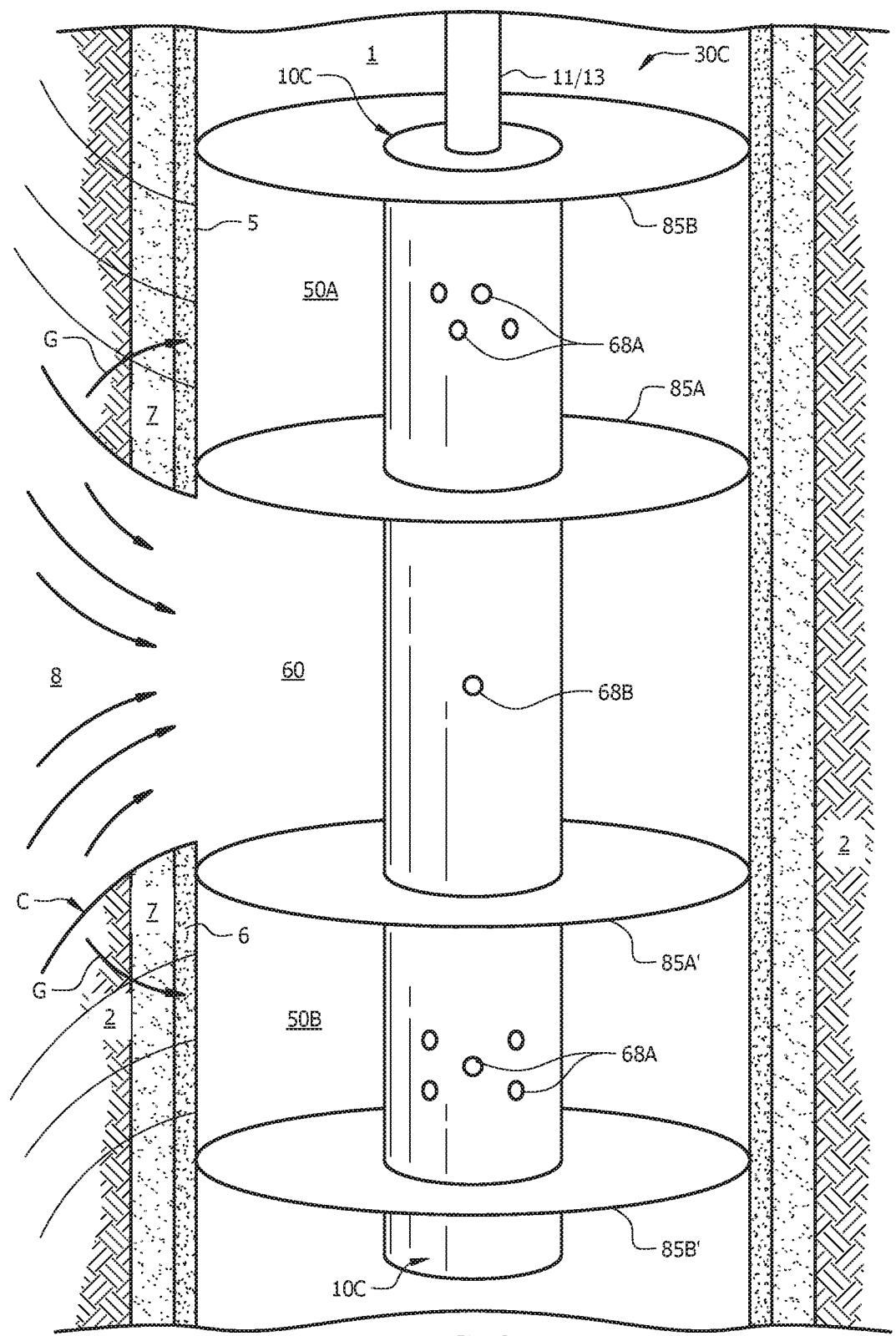
FIG. 8 is a schematic of a focused sampling system.

A focused sampling system 30 of this disclosure can comprise a multiple (e.g., dual) packer design, wherein the component of the focused sampling system 30 that contacts sidewall 5 of wellbore 1 does not include a focused sampling probe, but includes multiple packers or sets of packers. In such a packer design, one or more first packers can define the sample zone 60, wherein the sample zone 60 is in fluid communication with the sample line inlet 61A of the sample line 61, and one or more second packers can define the guard zone(s) 50, wherein the guard zone(s) 50 is in fluid communication with the guard line inlet 51A of the guard line 51. For example, FIG. 8 is a schematic of a focused sampling system 30C comprising downhole tool 10C. Focused sampling system 30C comprises, as component 20 (FIG. 1) that contacts sidewall 5 during operation, a first set of packers comprising first upper packer 85A and first lower packer 85A' and a second set of packers including second upper packer 85B and second lower packer 853. When deployed, first upper packer 85A is located within wellbore 1 above first lower packer 85A', second upper packer 85B is located within wellbore 1 above first upper packer 85A, and second lower packer 85B' is located within wellbore 1 below first lower packer 85A'. When deployed, the packers of the first packer set and the second packer set extend through mudcake 6 and contact sidewall 5 of wellbore 1, thus preventing flow of fluid within wellbore 1 from above or below the packer vertically past the packer. (Although described as "above" and "below", it is to be understood and will be readily apparent to those of skill in the art that a dual probe configuration, such as described with reference to FIG. 5, a probe packer configuration, such as described with reference to FIG. 7 and the dual packer set configuration, such as described with reference to FIG. 8 can be utilized in non-vertical wellbores 1.)

In the dual packer set configuration of FIG. 8, first upper packer 85A and first lower packer 85A' (e.g., of the first packer set) define the sample zone 60. Sample zone 60 is in fluid communication with the sample line inlet 61A of the sample line 61. Second upper packer 85B and second lower packer 85B' (e.g., of the second packer set) define the guard zone 50. In this configuration, guard zone 50 includes upper guard zone 50A, including the annulus around the body of formation tester 10C between second upper packer 85B and first upper packer 85A, and lower guard zone 50B, including the annulus around formation tester 10C between first lower packer 85A' and second lower packer 853. Guard zone 50 (e.g., upper guard zone 50A and/or lower guard zone 50B) is in fluid communication with the guard line inlet(s) 51A of the guard line(s) 51. One or more guard zone fluid inlets 68A along downhole tool 10C provide passage for fluid from guard zone 50 (e.g., upper guard zone 50A and/or lower guard zone 50B) into guard line inlet(s) 51A of the guard line(s) 51. One or more sample zone fluid inlets 68B along downhole tool 10C provide passage for fluid from sample zone 60 into sample line inlet 61A of sample line 61.

(First) upper packer 85A, (first) lower packer 85A', second upper packer 85B and second lower packer 85B' of FIG. 7 and FIG. 8 can be referred herein to as "focused sampling packers."

As noted hereinabove, a focused sampling system 30 of this disclosure can further comprise a restrictor valve $V_R$ positioned on or upstream of the sample line, a restrictor valve positioned on or upstream of the guard line, or both. The restrictor valve $V_R$ is operable to allocate flow of fluid from the guard zone(s) 50 into the guard line 51 and/or flow of fluid from the sample zone 60 into the sample line 61, such that a ratio $Q_G/Q_S$ of the flow rate $Q_G$ of fluid into the guard line 51 and the flow rate Qs of fluid into the sample line 61 is in a desired range. For example, one or more valve restrictors $V_R$ can be utilized to provide a flow ratio $Q_G/Q_S$ in a range of from about 2:1 to about 1:2, from about 2:1 to about 1:1, or from about 1:1 to about 1:2. One or more valve restrictors $V_R$ can be utilized to provide a flow ratio $Q_G/Q_S$ of greater than or equal to about 1:1, 1.5:1, or 2:1. The one or more flow restrictors $V_R$ can provide for the flow of fluid from the guard zone(s) 50 to be greater than the flow of fluid from the sample zone 60. The valve restrictor(s) enable allocation of flow of fluid from guard zone(s) 50 through guard line 51 and flow of fluid from sample zone 60 through sample line 61 at a desired flow rate ratio $Q_G/Q_S$, as discussed further hereinbelow. In embodiments, sample line volume $V_S$ is greater than a guard line volume $V_G$, wherein the sample line volume $V_S$ is a volume from the sample line inlet 61A to the sample line outlet 61B, and wherein the guard line volume $V_G$ is a volume from the guard line inlet(s) 51A to the guard line outlet 51B. The one or more restrictor valves $V_R$ can be variably controlled restrictor valves that can be manually or automatically (e.g., when deployed downhole) adjusted to provide a desired flow rate of fluid therethrough. Restrictor valve $V_R$ can be any restrictor operable to control the relative pressure differential and hence flow rate ratio between the sample zone 60 and the guard zone(s) 50 (e.g., between inner concentric ring 43A and outer concentric ring 43B of the probe 40A or 40B of FIG. 6A and FIG. 6B, respectively). A lower pressure differential and hence lower flow rate can generally be considered favorable for the sample zone 60 (inner concentric ring 43A). The restrictor valve $V_R$ can be a variable or static flow restrictor.

A focused sampling system of this disclosure can further comprise one or more dead volumes 45 in fluid communication with the sample line 61. The one or more dead volumes 45 can be online or offline dead volumes, meaning fluid in sample line 61 flows through the one or more dead volumes ("online") or does not flow through the one or more dead volumes ("offline") during a pre-sampling time period (discussed further hereinbelow). The one or more dead volumes 45 can include a first dead volume and a second dead volume in series along the sample line 61. The one or more dead volumes 45 provide a total dead volume $V_{TOT}$. In embodiments, the total dead volume $V_{TOT}$ is greater than or equal to a total sample volume of the one or more sample chambers 90.

The ideal size (e.g., total volume or $V_{TOT}$) of the one or more dead volume(s) 45 can be twice as large as the sample volume (e.g., a total volume of the one or more sample chambers 90) plus the flow line volume between the one or more dead volumes 45 and the one or more sample chambers 90. For example, without limitation, if the sample volume of the one or more sample chambers 90 is 1 liter and the flow line volume between the one or more dead volumes 45 and the one or more sample chambers 90 is 30 mL, the ideal total dead volume $V_{TOT}$ can be equal to or greater than 2.03L. The total dead volume $V_{TOT}$ provided by the one or more dead volumes 45 can be less than the sample size (e.g., the volume of the one or more sample chambers 90). In such instances, a clean fluid cone C flushed during the combined pumpout (e.g., the clean fluid cone C provided during pumping at step 103 described hereinbelow with reference to FIG. 12) can be used to supply the cleaner fluid to the one or more sample chambers 90. The total dead volume (e.g., $V_{TOT}$) provided by the one or more dead volumes 45 can be sufficiently large to overcome fluid compressibility issues with respect to the sample volume (e.g., the total volume of the one or more sample chambers 90) when filling the one or more sample chambers 90 with overpressure.

Figure 5:
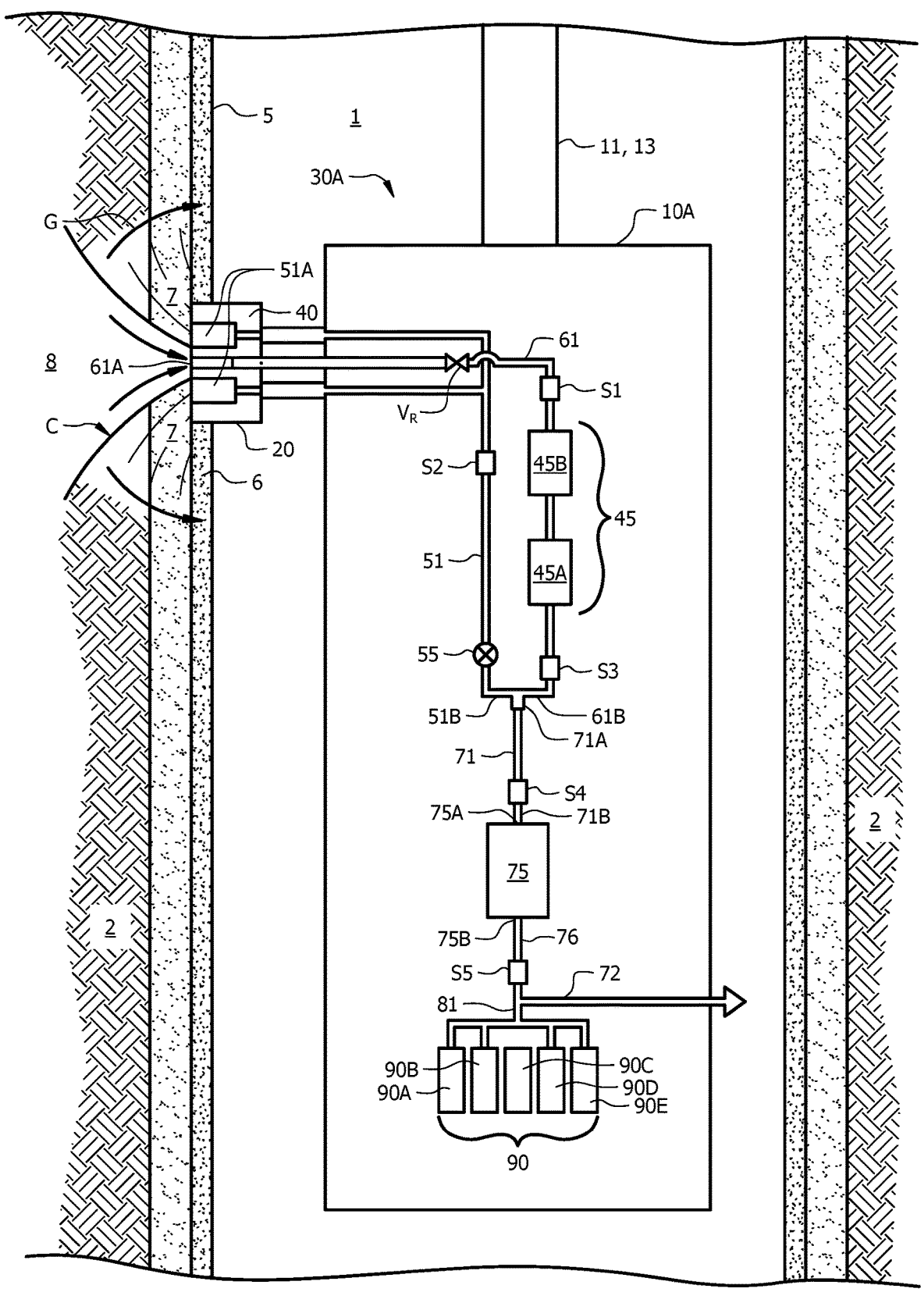
FIG. 5 is a schematic of a focused sampling system.
Figure 6A:
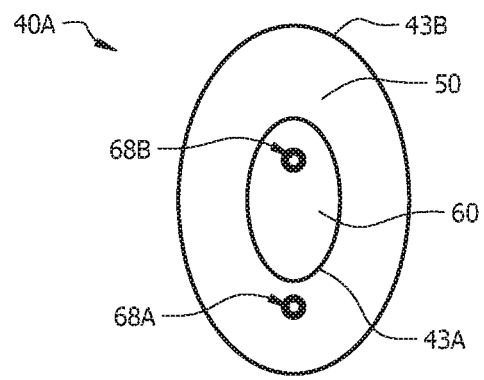
FIG. 6A is a schematic end view of a focused sampling probe.
Figure 6B:
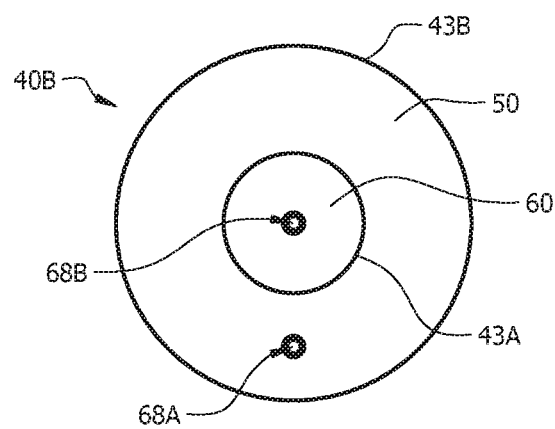
FIG. 6B is a schematic end view of a focused sampling probe.

The total dead volume can be divided between two dead volumes (such as depicted in FIG. 5) with a restriction optionally containing a check valve $V_C$ therebetween. The use of two dead volumes providing $V_{TOT}$ can prevent the direct mixing of the two dead volumes. As fluid flows from the inner portion (e.g., the center) of the formation flow cone C (FIG. 5; described further hereinbelow), as clean fluid cone C collapses after closing of flow restrictor 55 (e.g., a guard line shutoff valve on guard line 51), the fluid may become dirtier as the one or more sample chambers 90 are filled. Therefore, after shutting the flow restrictor 55 on the guard line 51 (e.g., after discontinuing flow of fluid from guard zone 50 into common line 71 at step 105 described with reference to FIG. 12 hereinbelow), rather than mix the fluid drawn into sample line 61 from sample zone 60 with a primary dead volume (e.g., a first dead volume 45A, described hereinbelow with reference to FIG. 5), the incoming fluid can be mixed with a secondary dead volume (e.g., second dead volume 45B) upstream of the primary dead volume. In this manner, the fluid within the secondary dead volume 45B then displaces the fluid in the first dead volume 45A. A gradient can exist across the dead volumes 45, with the dirtiest (e.g., most contaminated) fluid at the inlet of the dead volume and the cleanest (e.g., least contaminated) fluid at the outlet of the dead volume in each of the one or more dead volumes 45. Accordingly, by utilizing two (or more) dead volumes 45, the cleanest fluid can be introduced into the one or more sample chambers 90. The secondary dead volume (e.g., second dead volume 45B of FIG. 5) can be divided into multiple dead volumes in order to optimize the gradient across the sample line 61 after the flow restrictor or "guard shutoff valve" 55 has been actuated (e.g., at step 105 described herein with reference to FIG. 12). Also the volume of the first dead volume (e.g., volume $V_A$ of first dead volume 45A of FIG. 5) can be increased in size, however, the greater this volume $V_A$, the longer it can take to flush before sampling (e.g., the flushing of step 106 described hereinbelow with reference to FIG. 12). The use of more than one dead volume 45 on the sample line 61 upstream of pump 75 can be utilized to optimize space within downhole tool 10 and/or to improve flushing noted above and further detailed hereinbelow.

As depicted in FIG. 5, focused sampling system 30A comprises a first dead volume 45A and a second dead volume 45B on sample line 61 between the sample line inlet 61A and the sample line outlet 61B. First dead volume 45A and second dead volume 45B can be in series. A check valve $V_C$ can be positioned between first dead volume 45A and second dead volume 45B. First dead volume 45A and second dead volume 45B can be provided by enlarged diameter sections of sample line 61 or chambers fluidly connected along sample line 61. Various online and offline configurations can be utilized for the one or more dead volumes 45, and such will be readily apparent to those of skill in the art with the help of this disclosure. For example, without limitation, the one or more dead volumes 45 can be provided by coiled tubing along sample line 61, expanded diameter sections of sample line 61, chambers fluidly connected with sample line 61, cylinders comprising hydraulically actuated pistons, or the like. A few such embodiments will now be described with reference to FIG. 9, FIG. 10, and FIG. 11.

Figure 9:
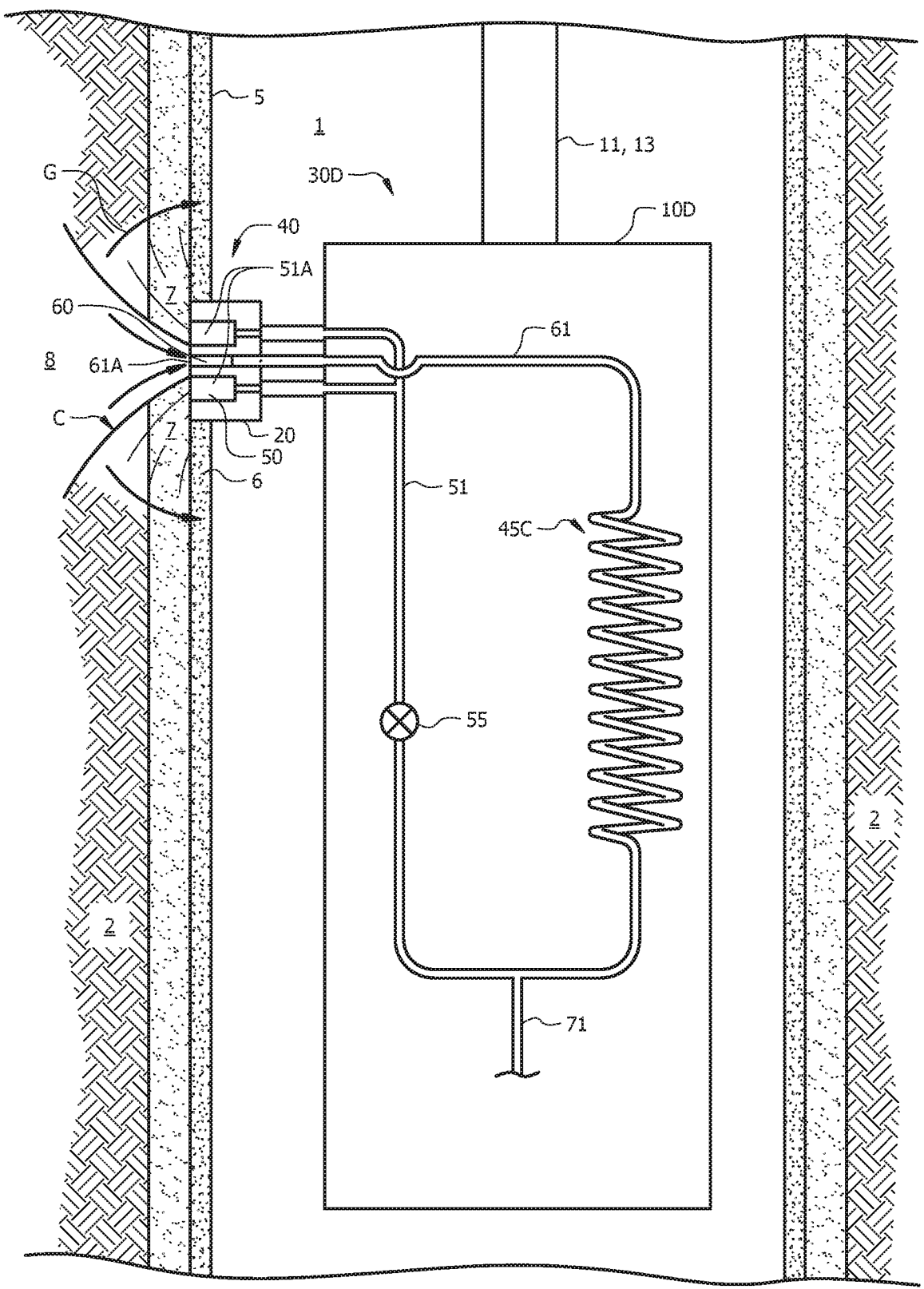
FIG. 9 is an abbreviated schematic of a focused sampling system comprising an alternative dead volume.

The dead volume 45 can comprise an extended tubing section, such as but not limited to coiled tubing. FIG. 9 is an abbreviated schematic of a focused sampling system 30D comprising a downhole tool 10D, comprising such an alternative dead volume. In FIG. 9, a dead volume 45C comprises coiled tubing. The coiled tubing dead volume 45C of FIG. 9 is depicted as an online dead volume. However, a coiled tubing dead volume, such as 45C, can be an offline coiled tubing dead volume. Coiled tubing dead volume 45C is positioned along sample line 61. Although depicted substantially as illustrated and described with reference to FIG. 5 (e.g., a dual probe configuration in which probe 40 provides the sample zone 50 and the guard zone 60), the remainder of focused sampling system 30D can comprise any arrangement of components as described herein. For example, a coiled tubing dead volume 45C can be employed with a focused sampling system having a probe packer configuration (e.g., with a probe defining sample zone 60 and one or more packers defining guard zone 50), as depicted and described hereinabove with reference to focused sampling system 30B of FIG. 7. Alternatively, a coiled tubing dead volume 45C can be employed with a dual packer configuration (e.g., with a first set of packers defining sample zone 60 and a second set of packers defining guard zones 50A and 50B), as depicted and described herein with reference to the FIG. 8.

Figure 10:
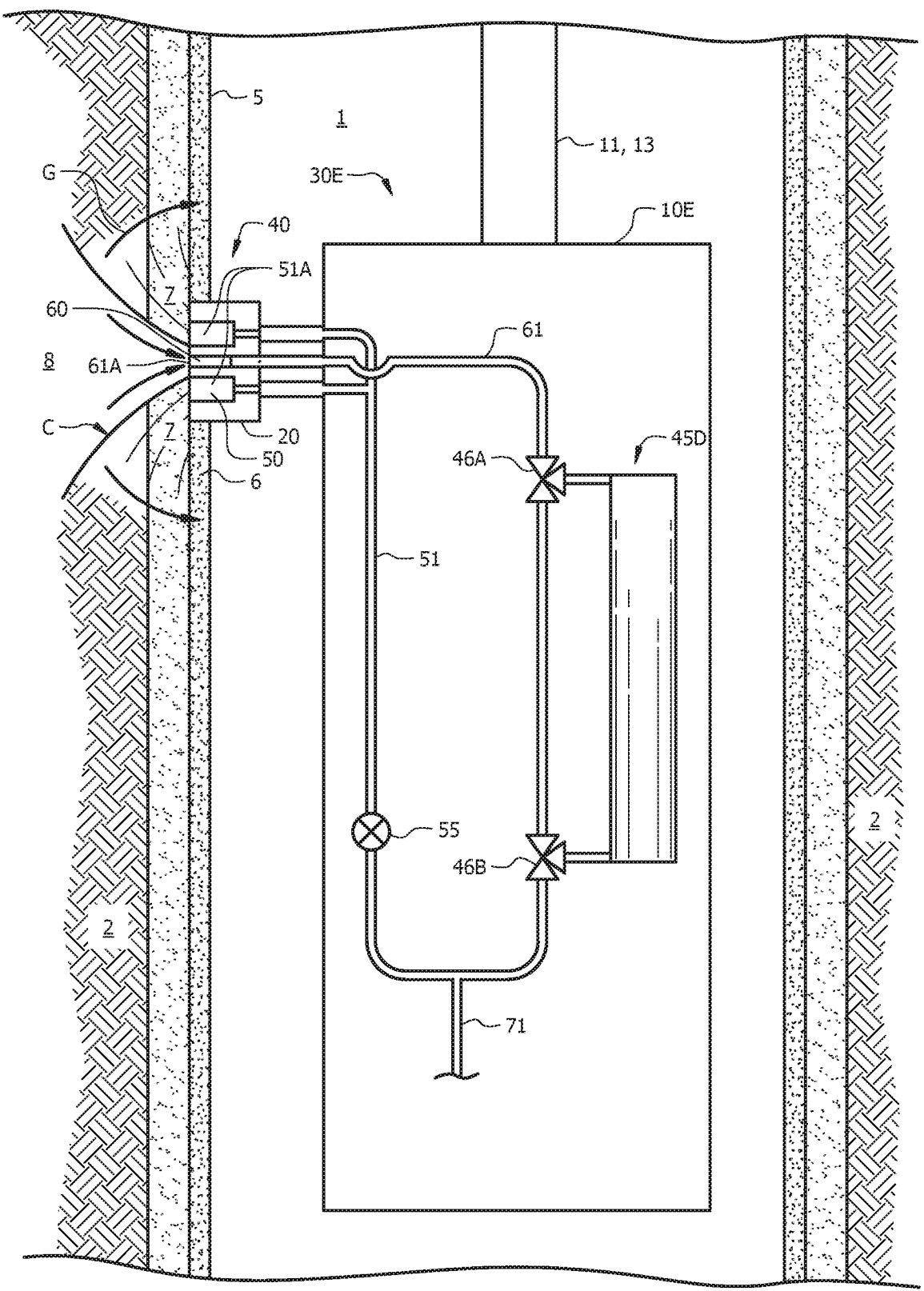
FIG. 10 is an abbreviated schematic of a focused sampling system comprising an alternative dead volume.

The one or more dead volumes 45 can comprise an offline dead volume on a side arm with respect to the sample line 61 through the pumpout (e.g., during formation of the clean cone C during step 103 described hereinbelow with reference to FIG. 12) and the flow of fluid in the sample line 61 can be diverted to the dead volume 45 at a later time after pumpout initiation when the flow cone C around sample zone 60 is cleaner than at the beginning of the pumpout. Such a configuration can avoid a slow flushing (e.g., a protracted flushing time, as described with reference to step 106 of FIG. 12 hereinbelow) of the dead volume 45 by filling the dead volume 45 with clean(er) fluid initially. FIG. 10 is an abbreviated schematic of a focused sampling system 30E comprising a downhole tool 10E comprising such an alternative dead volume. In FIG. 10, a dead volume 45D comprises a "side" chamber fluidly connected with sample line 61. Dead volume 45D can be divided into two side chambers in series (similar to first dead volume 45A and second dead volume 45B of FIG. 5). A first switch valve 46A and/or second switch valve 46B can be operable to direct flow of fluid in sample line 61 into or around (bypassing) dead volume 45D. The side chamber dead volume 45D of FIG. 10 is depicted as an online dead volume. However, a side chamber dead volume, such as 45D, can be utilized as an offline or online side chamber dead volume. Although the remainder of focused sampling system 30E is depicted substantially as illustrated and described with reference to FIG. 5 (e.g., a dual probe configuration in which probe 40 provides the sample zone 60 and the guard zone 50), the remainder of focused sampling system 30E can comprise any arrangement of components as described herein. For example, a side chamber dead volume 45D can be employed with a focused sampling system having a probe packer configuration (e.g., with a probe defining sample zone 50 and one or more packers defining guard zone 60), as depicted and described herein with reference to focused sampling system 30B of FIG. 7. Alternatively, a side chamber dead volume 45D can be employed with a dual packer configuration (e.g., with a first set of packers and a second set of packers defining sample zone 60 and guard zones 50A and 50B), as depicted and described herein with reference to FIG. 8.

Figure 11:
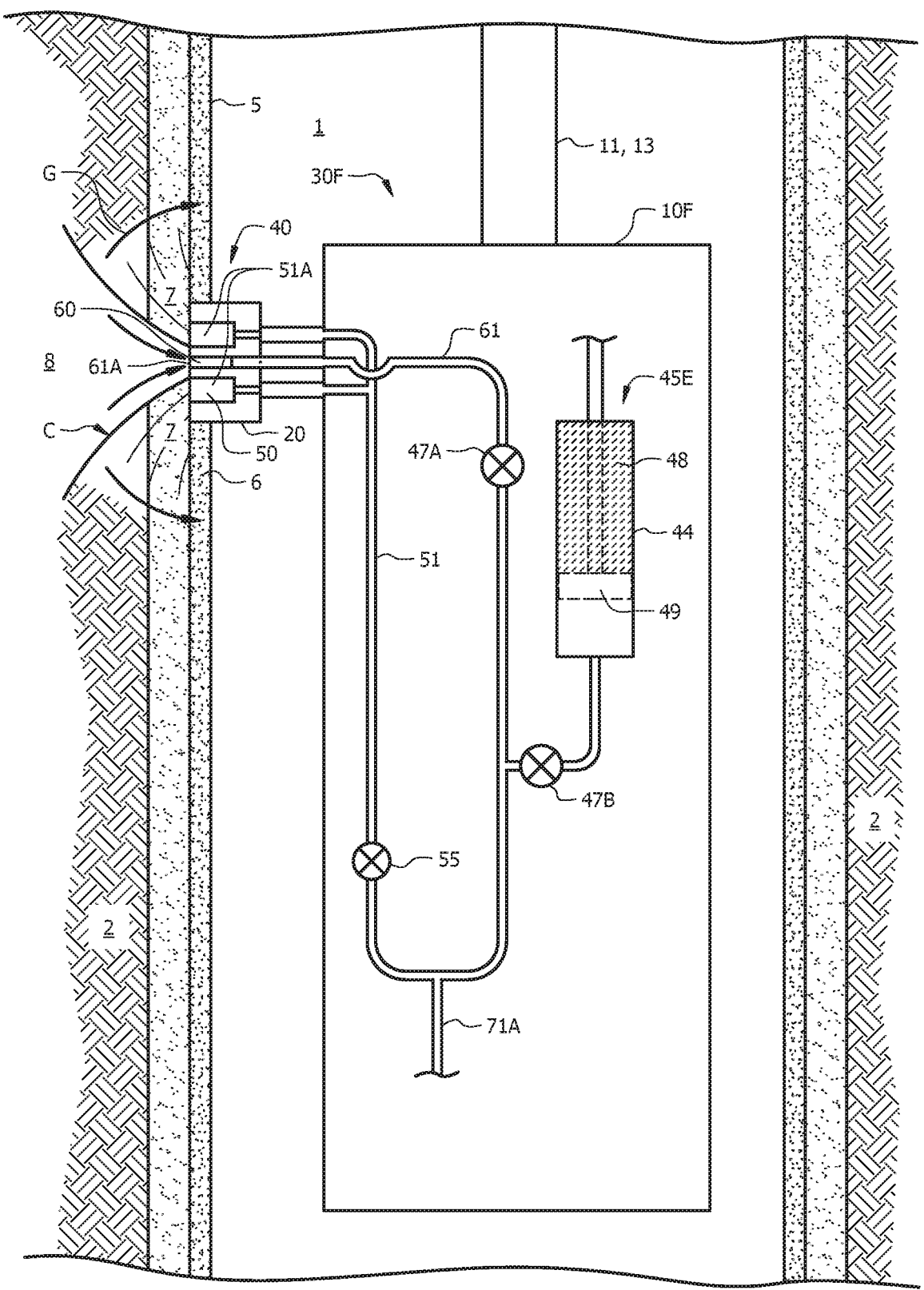
FIG. 11 is an abbreviated schematic of a focused sampling system comprising an alternative dead volume.

The dead volume(s) 45 can comprise a cylinder with a piston actuated when filling the one or more sample chambers 90. FIG. 11 is an abbreviated schematic of a focused sampling system 30F comprising a downhole tool 10F comprising such an alternative dead volume. In FIG. 11, a dead volume 45E comprises a cylinder comprising piston 49, hydraulically actuatable by a hydraulic fluid 48 (and a pump, not shown in FIG. 11), that is fluidly connected with sample line 61. A first valve 47A and/or second valve 47B can be operable to direct flow of fluid in sample line 61 into dead volume 45E or prevent fluid flow thereto. The dead volume 45E of FIG. 11 is operable as an offline dead volume. However, a hydraulic piston dead volume, such as 45E, can be utilized as an online dead volume. Although the remainder of focused sampling system 30F is depicted substantially as illustrated and described with reference to FIG. 5 (e.g., a dual probe configuration in which probe 40 provides the sample zone 50 and the guard zone 60), the remainder of focused sampling system 30F can comprise any arrangement of components as described herein. For example, a hydraulic piston dead volume 45E can be employed with a focused sampling system having a probe packer configuration (e.g., with a probe defining sample zone 50 and one or more packers defining guard zone 60), as depicted and described herein with reference to focused sampling system 30B of FIG. 7. Alternatively, a hydraulic piston dead volume 45E is employed with a dual packer configuration (e.g., with packers defining sample zone 60 and guard zones 50A and 50B), as depicted and described herein with reference to FIG. 8.

As noted hereinabove, a focused sampling system 30 of this disclosure comprises one or more sample chambers 90. For example, focused sampling system 30A of FIG. 5 comprises first sample chamber 90A, second sample chamber 90B, third sample chamber 90C, fourth sample chamber 90D, and fifth sample chamber 90E. Valves (not shown in FIG. 5) can be utilized to direct the flow of fluid from pump outlet line 76 into discard line 72 during a pre-sampling time period, including during a flushing time period, and to direct the flow of fluid from pump outlet line 76 into the one or more sample chambers 90 during a sampling time period. The pre-sampling time period, the flushing time period, and the sampling time period are described further hereinbelow with reference to FIG. 12.

Although depicted as downstream of pump 75, the one or more sample chambers 90 may be positioned at various positions within a focused sampling system 30 of this disclosure. For example, one or more sample chambers 90 can be positioned on a sampling line 81 fluidly connected with common line 71 upstream of pump 75.

Each of the one or more sample chambers 90 can be a sample chamber such as known to those of skill in the art. For example, the sample chambers 90 can comprise a bottle, and/or can contain a piston therein and be pressurized during sample filling. It will be appreciated that a variety of one or more sample chambers 90 may be used. The one or more sample chambers 90 can be interconnected with flowlines that extend to other of the one or more sample chambers 90, other portions of the downhole tool 10, the borehole 1 and/or other charging chambers. Preferably, the one or more sample chambers 90 are positioned to collect clean fluid. Moreover, it is desirable to position the one or more sample chambers 90 for efficient and high quality receipt of clean formation fluid. Fluid from the sample line 61, the guard line 51, the common line 71, the sampling line 81, or a combination thereof may be collected in one or more sample chambers 90 and/or dumped into the borehole 1. Furthermore, there is no requirement that a sample chamber 90 be included in a focused sampling system 30 of this disclosure. For example, such a focused sampling system absent any sample chambers 90 can be operable to determine properties of the clean sample line 61 fluid (which can be utilized for formation evaluation) without actually taking a sample thereof into a sample chamber 90.

As noted hereinabove, a focused sampling system 30 of this disclosure comprises one or more fluid ID sensors S positioned on the guard line 51, the sample line 61, the common line 71, or a combination thereof. For example, in FIG. 5, focused sampling system 30A comprises first fluid ID sensor S1 and third fluid ID sensor S3 located toward sample line inlet 61A and sample line outlet 61B of sample line 61, respectively, second fluid ID sensor S2 on guard line 51, fourth fluid ID sensor S4 on common line 71, and fifth fluid ID sensor S5 on pump outlet line 76. One or more fluid ID sensors S can be located on any combination of the guard line 51, the common line 71 upstream of pump 75, the pump outlet line 76 downstream of pump 75, the sampling line 81, or a combination thereof.

The one or more fluid ID sensors S can comprise pressure gauges, fluid analyzers, or the like. For example, pressure gauges may be connected to sample line 61 and guard line 51 to measure parameters therebetween, such as differential pressure. Such sensors may be located at other positions along any of the flowlines of the focused sampling system, as desired.

The one or more fluid ID sensors S (sometimes referred to herein as fluid monitoring devices) can be used to determine downhole parameters, such as, without limitation, content, contamination levels, chemical content (e.g., percentage of a certain chemical/substance), hydro mechanical (viscosity, density, percentage of certain phases, or the like), electromagnetic (e.g., electrical resistivity), thermal (e.g., temperature), dynamic (e.g., volume or mass flow), optical (absorption or emission), radiological, pressure, temperature, salinity, pH, radioactivity (gamma, neutron and/or spectral energy), carbon content, clay composition and content, oxygen content, and/or other data about the fluid and/or associated downhole conditions. One or more fluid ID sensors S can be utilized to collect optical measurements, such as optical density. Sensor data from the one or more fluid ID sensors S may be collected, transmitted to the surface 4 (e.g., surface of the earth or a platform) and/or processed downhole. Pressure gauges may be used, for example, to compare pressure levels in the sample line 61 and guard line(s) 51 for fault detection, or for other analytical and/or diagnostic purposes. Measurement data may be collected, transmitted to the surface 4 and/or processed downhole. This data, alone or in combination with additional data from the one or more fluid ID sensors S can be used to determine downhole conditions and/or make decisions (e.g., determine when to initiate sampling via steps 105, 106, and/or 107 described with reference to FIG. 12 hereinbelow). The one or more fluid ID sensors S can be operable to determine, without limitation, density, viscosity, bubble point, compressibility, capacitance, resistivity, acoustic, optical, mass spectroscopy, chromatography, NMR, nuclear, or a combination thereof.

While described as one or more fluid ID sensors S, other fluid monitoring devices, such as gauges, meters, sensors and/or other measurement or equipment can be incorporated into a focused sampling system 30 of this disclosure. Such equipment can be utilized to determine various properties of the fluid, such as temperature, pressure, composition, contamination and/or other parameters known to those of skill in the art. A controller can be included in focused sampling system 30 to take information from the one or more fluid ID sensors S and send signals in response thereto to alter the flow of fluid into the sample line 61 via sample zone 60, into the guard line(s) 51 via the guard zone(s) 50, into the discard line 72, and/or into the sampling line 81 of focused sampling system 30. Such a controller can be located in other parts of the downhole tool 10 and/or a surface system located at surface 4 for operating various components of the focused sampling system 30.

The one or more sample chambers 90 and/or one or more sensors S, such as a fluid analyzer, can be positioned near a probe 40/40A and/or upstream of the pump 75. It can be beneficial to sense fluid properties from a point closer to the subsurface formation 2, or the source of the fluid. Accordingly, it can be beneficial to test and/or sample upstream of the pump 75. Pump 75 typically agitates the fluid passing therethrough. Such agitation can spread the contamination to fluid passing through the pump and/or increase the amount of time before a clean sample may be obtained. By testing and/or sampling upstream of the pump 75, such agitation and spread of contamination may be reduced and/or avoided.

A focused sampling system 30 (e.g., 30A/30B/30C/30D/30E/30F) of this disclosure can comprise: a sample line 61 having a sample line inlet 61A and a sample line outlet 61B and containing fluid from a sample zone 60 of a subsurface formation 2 passing through the sample line 61 at a sample line fluid flow $Q_S$ allocated from the subsurface formation 2 into the sample line 61; a guard line 51 having a guard line inlet 51A and a guard line outlet 51B and containing fluid from a guard zone 50 of the subsurface formation 2 passing through the guard line 51 at a guard line fluid flow $Q_G$ allocated from the subsurface formation 2 into the guard line 51; a common line 71 having a common line inlet 71A and a common line outlet 71B, wherein the common line inlet 71A is fluidly connected with the sample line outlet 61B and the guard line outlet 51B and has a common line fluid flow $Q_C$ comprising the guard line fluid flow $Q_G$ allocated from the guard zone 50 into the guard line 51 and the sample line fluid flow $Q_S$ allocated from the sample zone 60 to the sample line 61, and wherein the common line outlet 71B is fluidly connected with a pump suction side inlet 75A of a pump 75; the pump 75, wherein a discharge side outlet 75B of the pump 75 is fluidly connected with a discard line 72 and a sampling line 81, and wherein the sampling line 81 is fluidly connected with one or more sample chambers 90; one or more fluid ID sensors S positioned on the guard line 61, the sample line 51, the common line 71, or a combination thereof; and a flow restrictor 55 operable to prevent flow of fluid from the guard line 51 to the common line 71 in a first configuration and allow flow of fluid from the guard line 51 to the common line 71 in a second configuration When the focused sampling system 30 is in a pre-sampling mode, during which a purity of the fluid in the sample line 61, as determined by the one or more fluid ID sensors S, is below the desired purity, the flow restrictor 55 is in the second configuration and thus allowing flow of fluid from the guard line 51 to the common line 71, and the focused sampling system 30 is configured such that pump 75 pumps fluid from the common line 71 to the discard line 72. When the focused sampling system 30 is in a sampling mode, initiated when a purity of the fluid in the sample line 61, as determined by the one or more fluid ID sensors S, is at or above the desired purity, the flow restrictor 55 is in the first configuration and thus preventing flow of fluid from the guard line 51 to the common line 71, and the focused sampling system 30 is configured such that the pump 75 pumps fluid from the common line 71 to the one or more sample chambers 90. Accordingly, via the focused sampling system 30 and method 100 of this disclosure, during a sampling (time) period, subsequent the pre-sampling (time) period, fluid is not drawn into the guard line(s) 51 via the guard zone(s) 50.

The focused sampling system 30 of this disclosure can further comprise a variety of additional devices, such as, without limitation, restrictors, diverters, processors and other devices for manipulating flow and/or performing various formation evaluation operations. Such additional devices will be apparent to those of skill in the art with the help of this disclosure and are not detailed herein.

It should be understood that the focused sampling system 30 of this disclosure can be implemented on any downhole tool 10 performing formation evaluation services regardless of the conveyance means of such downhole tool, without departing from the scope of the present disclosure. Thus, the downhole tool 10 comprising the focused sampling system 30 of this disclosure can be used for obtaining clean reservoir fluid (e.g., liquid and/or gas) during sampling applications using, for example, downhole tools 10 on drill pipe (i.e., formation evaluation and/or reservoir sampling capabilities incorporated on a drill string), as well as, without limitation, wireline systems.

Figure 12:
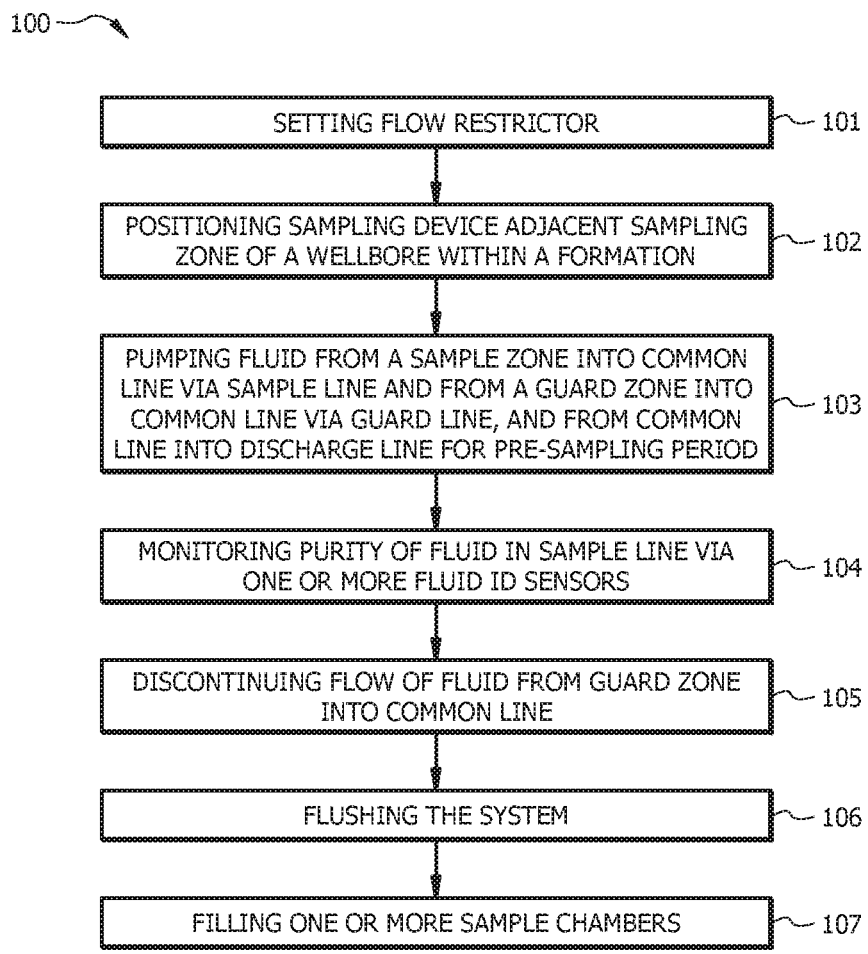
FIG. 12 is a flow chart of a method of focused sampling.

A method of focused sampling via the focused sampling system 30 of this disclosure described herein will now be provided with reference to FIG. 12, which is a flow chart of a method 100 of focused sampling, according to embodiments of this disclosure.

Focused sampling method 100 comprises: positioning a focused sampling system 30 as described hereinabove adjacent the sidewall 5 of wellbore 1 within a formation 2 at step 102; pumping fluid from the sample zone 60 of the formation 2 into the common line 71 via the sample line 61 and from the guard zone 50 of the formation 2 into the common line 71 via the guard line 51, and from the common line 71 into the discard line 72 for a pre-sampling period in which the flow restrictor 55 is in the second configuration, allowing flow of fluid from the guard line 51 to the common line 71 at step 103; monitoring a purity of the fluid in the sample line 61 via the one or more fluid ID sensors S at step 104; upon detecting that the purity of the fluid in the sample line 61 is at or above a desired purity: discontinuing flow of fluid from the guard zone 50 into the common line 71 by configuring the flow restrictor 55 in a first configuration in which flow of fluid from guard line 51 to common line 71 is prevented at step 105; and filling the one or more sample chambers 90 by pumping fluid from the common line 71 into the one or more sample chambers 90 at step 107.

The method comprises positioning a focused sampling device or system 30 (e.g., focused sampling system 30A-30F) as described hereinabove within a wellbore 1 within a formation 2 at step 102. As detailed hereinabove, the focused sampling device 30 comprises: a sample line 61 having a sample line inlet 61A and a sample line outlet 61B; a guard line 51 having a guard line inlet 51A and a guard line outlet 51B; a common line 71 having a common line inlet 71A and a common line outlet 71B, wherein the common line inlet 71A is fluidly connected with the sample line outlet 61B and the guard line outlet 51B, and wherein the common line outlet 71B is fluidly connected with a pump suction side inlet 75A of a pump 75; the pump 75, wherein a discharge side outlet 75B of the pump 75 is fluidly connected with a discard line 72 and a sampling line 81, wherein the sampling line 81 is fluidly connected with one or more sample chambers 90; one or more fluid ID sensors S positioned on the guard line 51, the sample line 61, the common line 71, or a combination thereof; and a flow restrictor 55 configured to prevent flow of fluid from the guard line 51 to the common line 71 in a first configuration and allow flow of fluid from the guard line 51 to the common line 71 in a second configuration. Positioning the focused sampling system 30 in the borehole 1 penetrating the subterranean formation 2 can be performed using at least one of a drill string 13 (FIG. 4) and a wireline 11 (FIG. 3).

The focused sampling system 30 can be a part of a downhole tool 10' of a wireline assembly or a bottom hole assembly (BHA) of a drilling tool 10", as depicted and described hereinabove with reference to FIG. 3 and FIG. 4, respectively. That is, downhole tools 10A-10F of FIG. 5 and FIG. 7 to FIG. 11, respectively, can comprise a wireline downhole tool 10', as depicted in FIG. 3, or a drilling tool 10", as depicted in FIG. 4. Those of ordinary skill in the art given the benefit of this disclosure will appreciate that the focused sampling system and method of this disclosure can be utilized in downhole applications other than conventional rotary drilling, and are not limited to land-based rigs. Examples of other downhole applications may involve the use of wireline tools (see, e.g., FIG. 2 or 3), casing drilling, coiled tubing, and other downhole tools.

As further depicted in FIG. 12, the focused sampling method 100 can further comprise, prior to positioning the focused sampling device 30 adjacent the sample zone 60 of the wellbore 1 within the formation 2, setting the flow restrictor 55 or another flow restrictor, such as a restrictor valve $V_R$ on sample line 61 and/or guard line(s) 51) of the focused sampling device 30 to provide a desired flow volume ratio $Q_G/Q_S$ between the guard line 51 and the sample line 61 at step 101. For example, restrictor valve $V_R$ and/or a flow restrictor 55, as described hereinabove, can be set to a desired value prior to positioning the focused sampling system 30 within wellbore 1. This can allow for allocating the flow of fluid from the guard zone 50 through guard line 51 and flow of fluid from the sample zone 60 through sample line 61. The desired flow volume ratio $Q_G/Q_S$ can be set to a value as described hereinabove. Alternatively, the desired flow ratio can be allocated subsequent positioning of the focused sampling system 30 downhole, for example, via an automatic or manual controller located at the surface 4 and in signal communication with the focused sampling system 30. The flow restriction provided by restrictor valve(s) $V_R$ and/or flow restrictors 55 can be set at step 101 based, for example, on an expected fluid mobility. For example, the ratio $Q_G/Q_S$ of the flow rate $Q_G$ of fluid from formation 2 into guard zone(s) 50 to the flow rate $Q_S$ of fluid from formation 2 into sample zone 60 can be set to about 2 or greater for highly mobile formation fluid. Restrictor valve(s) $V_R$ can be variably controlled to optimize cleanup (e.g., formation of clean formation fluid cone C) based on the permeability of formation 2 and/or a cleanup response. The greater the permeability, the greater the restriction of fluid flow to sample line 61 via sample zone 60 provided by a restrictor valve $V_R$ on sample line 61 (and/or a flow restrictor 55 on sample line 61) may be. Alternatively, the cleanup rate as measured by one or more fluid sensors S can be utilized to optimize the flow rate ratio $Q_G/Q_S$ by means such as, but not limited, to simplex optimization.

Once the downhole tool 10 comprising the focused sampling system 30 of this disclosure is positioned downhole within wellbore 1, probe 40/40A as described with reference to FIG. 5 and FIG. 6, and/or packers (e.g., upper or first upper packer 85A and lower or first lower packer 85A' as described with reference to FIG. 6 and FIG. 7 and/or second upper packer 85B and second lower packer 85B' as described hereinabove with reference to FIG. 7) can be positioned (e.g., extended or inflated) against sidewall 5 of wellbore 6 to provide sample zone 60 and guard zone(s) 50 as described hereinabove with reference to FIG. 5, FIG. 7 and FIG. 8. For example, a probe 40 as described herein can be extended from downhole tool 10 comprising focused sampling system 30 for engagement of the probe 40 with wellbore sidewall 5. The packer(s) are operable for sealing with the wellbore sidewall 5. The packer(s) contact the wellbore sidewall 5 and form a seal with the mudcake 6 lining the wellbore 1. As described with reference to FIG. 1 and FIG. 2, the mudcake 6 seeps into the wellbore wall 5 and creates an invaded zone 7 about the wellbore 1. The invaded zone 7 contains mud and other wellbore fluids that contaminate the surrounding formation(s) 2, including the formation 2 and a portion of the virgin formation fluid 8 contained therein.

Subsequent positioning of the focused sampling device 30 at step 102, the method comprises, at step 103, pumping fluid from the sample zone 60 of the formation 2 into the common line 71 via the sample line 61 and from the guard zone 50 of the formation 2 into the common line 71 via the guard line 51, and from the common line 71 into the discard line 72 for a pre-sampling period in which the flow restrictor 55 is in the second configuration, allowing flow of fluid from the guard line 51 to the common line 71. As depicted in FIG. 1, prior to the pumping of fluid at step 103 (which step 103 can also referred to herein as "pumpout"), the invaded or contaminated zone 7 extends vertically beyond sidewall 5 a distance into formation 2. With reference to FIG. 2 and FIG. 5, during pumping at step 103, a central flow cone C of clean formation fluid 8 is created in formation 2, while a mud filtrate gradient from virgin fluid 8 to contaminated fluid 9 extends from the boundaries of flow cone C to sidewall 5 of wellbore 1, as indicated by gradient arrow G. The pumpout of step 103 positions the sample zone 60 within the clean flow cone C, such that uncontaminated formation fluid is eventually drawn in through sample line 61, while contaminated fluid is drawn into guard line 51 via the guard zone(s) 50 positioned in the contaminated zone 7. Clean formation fluid from the center flow cone C can subsequently be utilized to displace fluid in sample line 61 and capture a sample (e.g., in the one or more sample chambers 90) before the flow cone C collapses. The ratio of the guard flow rate $Q_G$ to the sample zone flow rate $Q_S$ can be allocated such that the flow of fluid from the guard zone 50 is greater than the flow of fluid from the sample zone 60. Step 103 can thus also be considered a step of creating a clean fluid flow cone C in the formation 2, wherein the clean fluid flow cone C is comprised of formation fluid in the center of the flow cone C and a gradient to filtrate (e.g., along gradient arrow G) occurs from the center of flow cone C to the sidewall 5 of wellbore 1). The gradient can be optimized by the use of a restrictor valve $V_R$ (or other flow restrictor, such as flow restrictor 55 on guard line 51) located on at least one of the sample line 61 and the guard line(s) 51. The method can further comprise optimizing the ratio $Q_G/Q_S$ of the flow rate $Q_G$ of fluid from formation 2 into guard zone 50 to the flow rate $Q_S$ of fluid from formation 2 into sample zone 60 by selection of the flow restrictor setting at step 101 and/or adjustments of the flow restriction during pumping at step 103 based on at least one fluid mobility fluid sensor measurement.

The method 100 further comprises, at step 104, monitoring a purity of the fluid in the sample line via the one or more fluid ID sensors S while continuing pumping as described at step 103. The monitoring at step 104 is utilized to determine when central cone C of clean formation fluid has been created within formation 2. The monitoring can be effected via a fluid ID sensor S (such as fluid ID sensor S1 and/or fluid ID sensor S3) on the sample line 61 in conjunction with a fluid ID sensor S (such as fluid ID sensor S2) on the guard line 51, a fluid ID sensor S (such as fluid ID sensor S4) on the common line 71, or both a fluid ID sensor S (such as fluid ID sensor S2) on the guard line 51 and a fluid ID sensor S (such as fluid ID sensor S4) on the common line 71. Monitoring the purity of the fluid in the sample line 61 via the one or more fluid ID sensors S further comprises comparing measurements obtained from a fluid ID sensor S (such as fluid ID sensor S1 and/or fluid ID sensor S3) on the sample line 61 with measurements obtained from a fluid ID sensor S (such as fluid ID sensor S2) on the guard line 51 and/or a fluid ID sensor S (such as fluid ID sensor S4) on the common line 71. Accordingly, monitoring at step 104 is utilized to decide when to acquire the sample(s) (e.g., in the one or more sample chambers 90) and/or perform analysis on the clean formation fluid based in part on at least one measurement of the one or more fluid ID sensors S. Monitoring at step 104 can comprise obtaining one or more fluid measurements from one or more fluid ID sensors on sample line 61 with or without comparison to fluid measurements obtained from one or more fluid ID sensors S on guard line 51 and/or common line 71 to calculate a drilling fluid filtrate contamination in the fluid in sample line 61.

As detailed further hereinbelow, once monitoring at step 104 determines that the fluid in sample line 61 has a desired contamination value (e.g., a desired purity), a sequence can be initiated to close the guard line 51 via flow restrictor 55 at step 105, (optionally) flush the common line 71 (and optionally dead volumes 45) at step 106, and fill the one or more sample chambers 90 at step 107.

Step 105 comprises, upon detecting that the purity of the fluid in the sample line 61 is at or above a desired purity (or the contamination is at or below a maximum contamination level) at step 104, discontinuing flow of fluid from the guard zone 50 into the common line 71 by configuring the flow restrictor 55 in the first (e.g., closed/restricted) configuration, such that the flow of fluid in common line 71 subsequently comprises solely the flow of fluid from sample line 61.

The method can further comprise flushing the focused sampling system 30 by passing a flush volume of fluid from the sample zone 60 of the formation 2 to the discard line 72 via the sample line 61 and the common line 71 at step 106. This flushing step 107 can be utilized to ensure that the system has been sufficiently cleaned (e.g., that any contaminated fluid downstream of a fluid ID sensor S that has indicated the presence pf clean fluid has been flushed out of the focused sampling system 30). The flush volume can be at least three, two, or one times a volume of fluid contained by the focused sampling device 30 between the sample line inlet 61A and the sample line outlet 61B.

The method 100 further comprises, at step 107 subsequent to the discontinuing of the flow of fluid from the guard zone 50 into the common line 71 at step 105 and/or subsequent to the optional flushing of the focused sampling system 30 at step 106, filling the one or more sample chambers 90 by pumping fluid from the common line 71 into the one or more sample chambers 90. The one or more samples can be acquired (e.g., introduced into the one or more sample chambers 90) based on timing with respect to the actuation of the flow restrictor 55 (e.g., guard line shutoff valve) on guard line 51 at step 105 of discontinuing of the flow of fluid from the guard zone 50 into the common line 71. The timing of introduction of clean formation fluid into the one or more sample chambers 90 can be determined at least in part with respect to a pump flow rate of pump 75. That is, based on the pump flow rate of pump 75, a flushing time period of step 106 and/or a sampling time period of step 107 can be determined.

For offline dead volumes 45, the sequence can be altered such that, upon detecting that the purity of the fluid in the sample line 61 is at or above a desired purity (or the contamination is at or below a maximum contamination level) at step 104, fluid flow can be diverted from the sample line 61 to the (previously offline, now online) dead volume(s) 45 whereby the dead volume(s) 45 is (are) flushed. Flushing the dead volume(s) 45 can be effected via flow through (e.g., via switch valves 46A and 46B for dead volume(s) 45D such as depicted in FIG. 10) or sufficient stroking of a piston (e.g., piston 49 of FIG. 11 and operation of valves 47A and 47B). After flushing of the dead volume(s) 45, step 105 of discontinuing the flow of fluid from the guard line(s) 61 into common line 71 can be effected (e.g., by closing the guard line 51 via flow restrictor 55) and fluid diverted from the dead volume(s) 45 via the sample line 61 to common line 71. Common line 71 can then be flushed at step 106 prior to taking one or more samples in the one or more sample chambers 90. Accordingly, in offline dead volume embodiments, flushing of the system at step 106 can be performed partially before and partially after step 105.

As noted hereinabove, a volume of at least one, two or three times a volume of a component (e.g., a volume of a dead volume 45, a total volume $V_{TOT}$ of the one or more dead volumes 45, a volume of common line 71) can be utilized to flush the component. For example, if a dead volume being flushed is 2 liters, flushing the dead volume 45 can comprise passing a flush volume of at least 2, 4, or 6 liters through the dead volume 45 to flush the dead volume 45 prior to sampling (e.g., taking a measurement with the one or more fluid ID sensors for formation evaluation and/or introducing sample fluid into the one or more sample chambers 90). If the common line 71 has a volume of 30 mL, flushing the common line 71 can comprise passing a flush volume of at least 30, 60, or 90 mL through the common line 71 to flush the common line 71.

A focused sampling method of this disclosure can further comprise discontinuing drilling prior to positioning the focused sampling device 30 within the wellbore 1 at step 102; retrieving the one or more sample chambers 90 from the wellbore subsequent the filling of the one or more chambers at step 107; continuing drilling within the formation subsequent the filling of the one or more chambers 90 at step 107; or any combination or repetition of one or more thereof. For example, focused sampling system 30 can be a component of a drilling tool 10" comprising a LWD or MWD drilling tool (e.g., as depicted in FIG. 4). In such applications, the focused sampling method can comprise discontinuing drilling prior to positioning the focused sampling device 30 within the wellbore 1 at step 102; continuing drilling within the formation 2 subsequent the filling of the one or more sample chambers 90 at step 107; or a combination or repetition of one or more thereof. In alternative applications, focused sampling system 30 is a component of a wireline tool 10' (as depicted, for example, in FIG. 3), and a focused sampling method of this disclosure further comprises retrieving the one or more sample chambers 90 from the wellbore 1 subsequent the filling of the one or more chambers 90 at step 107 by retrieving the wireline tool 10' from the wellbore 1. Such a method can further comprise inserting a drill string 13 into wellbore 1, and continuing drilling within the formation 2 subsequent the filling of the one or more chambers 90 at step 107 and the removal thereof from wellbore 1. Various combinations and arrangement of steps described herein will be apparent to those of skill in the art upon reading this disclosure and are intended to be included herein.

As noted hereinabove, the focused sampling device 30 can further comprise one or more dead volumes 45 fluidly connected with the sample line 61. In such instances, filling the one or more sample chambers 90 by pumping fluid from the common line 71 into the one or more sample chambers 90 at step 107 can comprise pumping fluid from the one or more dead volumes 45 into the common line 71 and from the common line 71 into the one or more sample chambers 90.

In embodiments comprising one or more dead volumes 45, wherein the one or more dead volumes 45 can be positioned offline, flushing the focused sampling system at step 106 can further comprise isolating the one or more dead volumes 45 from the fluid flow path (e.g., from sample line inlet 61A to sample line outlet 61B) prior to flushing the focused sampling system 30 at step 106 and de-isolating (e.g., putting back into the flow path of fluid from sample line inlet 61A to sample line outlet 61B) the one or more dead volumes 45 from the fluid flow prior to filling the one or more sample chambers 90 at step 107. For example, with reference to FIG. 10, switch valve 46A and/or switch valve 46B can be operated to allow the flow of fluid from sample line 61 into dead volume 45D during the pumping at step 103 and/or the monitoring at step 104. Subsequently or concurrently with the discontinuing of the flow of fluid from guard zone 50 into common line 71 at step 105, switch valve 46A and/or switch valve 46B can be positioned to prevent flow of fluid from sample line 61 into dead volume 45D. In this manner, a focused sampling system (e.g., focused sampling system 30E of FIG. 10) can be flushed with a smaller volume of fluid than would be required to flush the focused sampling system without isolating the one or more dead volumes from the flow path during the flushing at step 106.

The one or more dead volumes 45 can be offline during the pumping at step 103, the monitoring at step 104, the discontinuing at step 105, and/or the flushing at step 106, and can be put online (e.g., in the fluid flow path from sample line inlet 61A to sample line outlet 61B) subsequent to or concurrently with the discontinuing at step 105 and/or the flushing at step 106. For example, with reference to FIG. 11, valve 47A can be open and valve 47B closed to prevent the flow of fluid from sample line 61 into dead volume 45E during the pumping at step 103 and the monitoring at step 104. Subsequently or concurrently with the discontinuing the flow of fluid from guard zone 50 into common line 71 at step 105 and/or the flushing at step 106, switch valve 46B can be opened and piston 49 actuated to fill dead volume 45E with fluid from sample line 61, whereafter valve 47B can be closed. Subsequent flushing of the focused sampling system 30F at step 106, switch valve 47A can be closed to prevent flow of fluid from dead volume 45E back toward formation 2, and valve 47A can be opened, whereby filling of the one or more sample chambers 90 at step 107 can be effected by actuating piston 49 to depress the fluid out of dead volume 45E into the one or more sample chambers 90. For example, the one or more dead volumes 45E can be offline dead volumes, and the method can further comprise, at step 105, upon detecting that the purity of the fluid in the sample line 61 is at or above the desired purity, diverting flow of fluid from the sample inlet 61A of the sample line 61 to the one or more dead volumes 45E.

Subsequent discontinuing flow of fluid from guard zone(s) 50 into common line 71 (e.g., actuating a restrictor 55 (e.g., a shutoff valve) in the guard line 51) at step 105, clean fluid in central fluid flow cone C is introduced to one or more sample chambers 90 before collapse of the flow cone C results in the introduction of filtrate from the invaded zone 7 along gradient arrow G into the one or more sample chambers 90. The one or more dead volumes 45 on sample line 61 upstream of common line 71 can be utilized to extend the time for collecting the one or more samples in the one or more sample chambers 90 prior to filtrate invasion into flow cone C and sample zone 60.

A focused sampling method of this disclosure can comprise: placing a formation fluid sampling device 30 adjacent a sampling zone in a wellbore 1 penetrating a subterranean formation 2; concurrently pumping, via a common pump 75 disposed within the sampling device 30, a sample flow of formation fluid in a sample flow line 61 from the subterranean formation 2 into the sampling device 30 and a guard flow of formation fluid in a guard flow line 51 from the subterranean formation 2 into the sampling device 30, wherein the guard flow rate $Q_G$ is greater than the sample flow rate $Q_S$ and forms a guard zone 50 around and adjacent the sample zone 60 within the sampling zone; during the concurrently pumping, analyzing the formation fluid in the sample flow line 61 to determine whether an amount of contaminant within the formation fluid in the sample flow line 61 has dropped below a threshold value; and, upon determining that the amount of contaminant within the formation fluid in the sample flow line 61 has dropped below a threshold value, decreasing or discontinuing the guard flow of the formation fluid in the guard flow line 51 and diverting the sample flow of the formation fluid in the sample flow line 61 to a sample chamber 90.

A focused sampling method of this disclosure can comprise: allocating flow of fluid from a guard zone 50 through a guard line 51 and flow of fluid from a sample zone 60 through a sample line 61, wherein the guard zone 50 is positioned at least partially concentrically about the sample zone 60 and wherein the guard zone 50 and the sample zone 60 are in fluid communication with a formation 2; pumping, via a common line 71, a combined flow of fluid from the formation 2 through to a discard line 72 for a pre-sampling time period until the flow allocated into the sample line 61 from the sample zone 60 comprises formation fluid 8 having a desired purity (or a contamination level below a maximum contamination level), wherein the combined flow comprises the flow of fluid allocated from the guard zone 50 into the guard line 51 and the flow of fluid allocated from the sample zone 60 into the sample line 61; subsequent the pre-sampling time period, discontinuing flow from the guard line 51 into the common line 71, such that the combined flow comprises only the flow of fluid from the sample line 61; and introducing the combined flow comprising the flow of fluid from the sample line 61 into one or more sample chambers 90.

The focused sampling method can further comprise, subsequent the discontinuing the flow from the guard line 51 into the common line 71, introducing the combined flow comprising the flow of fluid from the sample line 61 to the discard line 72 via the combined flow line 71 for a flushing time period prior to the introducing the combined flow comprising the flow of fluid from the sample line 51 into the one or more sample chambers 90. As noted hereinabove, a sample line volume $V_S$ of the sample line 61 can be greater than a guard line volume $V_G$ volume of the guard line 51, wherein the sample line volume $V_S$ is a volume from the sample line inlet 61A to the sample line outlet 61B, and wherein the guard line volume $V_G$ is a volume from the guard line inlet 51A to the guard line outlet 51B.

As described hereinabove, the method can further comprise one or more dead volumes 45 in fluid communication with the sample line 61. The one or more dead volume 45 can include a first dead volume 45A and a second dead volume 45B in series along the sample line 61 between the sample line inlet 61A and the sample line outlet 61B, wherein the one or more dead volumes provide a total dead volume $V_{TOT}$.

The method can further comprise, subsequent the discontinuing the flow from the guard line 51 into the common line 71, introducing the combined flow comprising the flow of fluid from the sample line 61 to the discard line 72 via the combined flow line 71 for a flushing time period prior to the introducing the combined flow comprising the flow of fluid from the sample line 61 into the one or more sample chambers 90, and wherein the flushing time period is a time sufficient to pass a volume of at least three times the total dead volume $V_{TOT}$ to the discard line 72.

As noted hereinabove, allocating can comprise selecting or adjusting a restrictor valve $V_R$ positioned on or upstream of the sample line 51, a restrictor valve $V_R$ positioned on or upstream of the guard line 61, or both. The restrictor valve $V_R$ can be a variably controlled restrictor valve. Discontinuing the flow from the guard line 51 into the common line 71 can comprise actuating a flow restrictor 55 (e.g., variable or static) on the guard line 51. The method can further comprise determining an end of the pre-sampling time by data received from one or more fluid ID sensors S positioned on the guard line 61, the sample line 51, the common line 71, or a combination thereof. The flow of fluid $Q_G$ from the guard zone 50 can be greater than the flow of fluid $Q_S$ from the sample zone 60 during the pumping, via the common line, of the combined flow of fluid from the formation 2 through to the discard line 72 for the pre-sampling time period.

Those of ordinary skill in the art will readily appreciate various benefits that may be realized by the present disclosure. Contamination in (e.g., LWD) sampling is a significant issue. Cleanup to acceptable contamination takes very long times with conventional focused sampling systems. Also because of the potential for active drilling fluid filtrate invasion, baseline contamination levels are generally higher than with a more established mudcake. Focused sampling is a technique used to both speed up the rate of sampling and obtain cleaner samples. Unfortunately, conventional focused sampling often requires two pumps and a relatively complicated plumbing system. The focused sampling system and method of this disclosure provides a technique to achieve an at least partially focused sample and obtain advantages of full focused sampling, but with a single pumpout system. Therefore, in embodiments, the focused sampling system and method of this disclosure can easily be retrofit into existing downhole tools (e.g., LWD samplers) with a simple (e.g., single pump) pumpout system. Via the focused sampling system and method of this disclosure, a degree of focused sampling conventionally effected with dual pumps can be provided (or approached) with a focused sampling system 30 comprising only a single pump.

According to this disclosure, during pumpout (e.g., at step 103 of FIG. 12), fluid is pulled through the guard zone(s) 50 and sample zone 60. Fluid can fill the one or more dead volumes 45 through the sample zone 60, whereby the fluid is drawn into focused sampling system 30 via the cleaner cross section of the fluid flow cone C. The more contaminated guard fluid from the dirtier outer portion of and/or outside the fluid flow cone C can be drawn into guard line 51 and thus bypasses sample line 61 and optionally one or more dead volumes 45 and commingles with the fluid in the sample line 61 after the one or more dead volumes 45 (e.g., in common line 71). Accordingly, a cleaner sample fluid is in reserve in the one or more dead volumes 45 for sampling. After the fluid in the sample line 61 is considered sufficiently clean by the one or more fluid ID sensors S at the monitoring of step 104, the restrictor 55 (e.g., shutoff valve) on the guard line 61 can be actuated at step 105. This shuts off flow from the guard zone 50 (e.g., an outer concentric ring 43B of probe 40), but fluid still flows from the sample zone (e.g., an inner concentric ring 43A of probe 40). The cross section of fluid from flow cone C entering the sample line 61 is initially cleaner than the cross section of fluid from the outer cone (e.g., in invaded zone 7 outside clean cone C), however, the clean flow cone C will collapse with time, after discontinuing the flow of fluid from guard zone 50 at step 105. The fluid from sample zone 60 (e.g., within the inner concentric ring 43A of dual probe configuration of FIG. 5 or within ring 43 of probe 40A of FIG. 7) will displace the fluid in the one or more dead volumes 45 being held in reserve for sampling. After a volume equal to or greater than the flow line volume between the one or more dead volumes 45 and the one or more sample chamber(s) 90 has been pumped through discard line 72, the fluid may be diverted into the one or more sample chambers 90. Accordingly, via the herein disclosed focused sampling system and method, a clean fluid can be obtained utilizing a single pump/pumpout system.

Conventional two pump and private line focused sampling double required capital and double downhole tool (e.g., the bottom hole assembly) space over existing non-focused sampling designs. The herein disclosed focused sampling system and method can utilize a modification to a conventional non-focused sampling device, optionally requiring only slightly more space, such as to achieve the desired dead volume and enables faster attaining of cleaner samples, approaching or equaling the performance of full focused sampling.

Herein disclosed are a focused sampling system and method for manipulating the flow of fluids through a downhole tool to reduce contamination entering and/or passing through the downhole tool. The herein disclosed focused sampling system and method are capable, with a single pump, of diverting contaminants away from clean formation fluid, and are operable for analyzing the fluid passing through flowlines of the downhole tool, manipulating the flow of fluid through the downhole tool, responding to detected contamination, removing contamination, separating virgin formation fluid from contaminated fluid, selectively collecting virgin fluid apart from contaminated fluid, optimizing the quantity and/or quality of formation fluid extracted from the formation for sampling, adjusting the flow of fluid according to sampling needs and/or contamination levels, controlling the sampling operation manually, automatically, and/or on a real-time basis, analyzing the fluid flows to detect contamination levels, estimating time to clean up contamination prior to taking one or more fluid samples, adjusting flowline ratios, determining contamination levels, and comparing flowline data to known or desired values.

The herein disclosed focused sampling system and method enable, with the use of a single pump, optimization of the testing and/or sampling process during formation evaluation. In some cases, such optimization may be in response to real time measurements, operator commands, pre-programmed instructions and/or other inputs.

ADDITIONAL DISCLOSURE

The following are non-limiting, specific embodiments in accordance with the present disclosure:

Embodiment A: A focused sampling method comprising: allocating flow of fluid from a guard zone through a guard line and flow of fluid from a sample zone through a sample line, wherein the guard zone is positioned at least partially concentrically about the sample zone and wherein the guard zone and the sample zone are in fluid communication with a formation; pumping, via a common line, a combined flow of fluid from the formation through to a discard line for a pre-sampling time period until the flow allocated into the sample line from the sample zone comprises formation fluid having a desired purity (or a contamination level below a maximum contamination level), wherein the combined flow comprises the flow of fluid allocated from the guard zone into the guard line and the flow of fluid allocated from the sample zone into the sample line; subsequent the pre-sampling time period, discontinuing flow from the guard line into the common line, such that the combined flow comprises only the flow of fluid from the sample line; and introducing the combined flow comprising the flow of fluid from the sample line into one or more sample chambers.

Embodiment B: The focused sampling method of Embodiment A further comprising, subsequent the discontinuing the flow from the guard line into the common line, introducing the combined flow comprising the flow of fluid from the sample line to the discard line via the combined flow line for a flushing time period prior to the introducing the combined flow comprising the flow of fluid from the sample line into the one or more sample chambers.

Embodiment C: The focused sampling method of Embodiment A or Embodiment B, wherein a sample line volume is greater than a guard line volume, wherein the sample line volume is a volume from the sample line inlet to the sample line outlet, and wherein the guard line volume is a volume from the guard line inlet to the guard line outlet.

Embodiment D: The focused sampling method of any of Embodiment A to Embodiment C further comprising one or more dead volumes in fluid communication with the sample line.

Embodiment E: The focused sampling method of Embodiment D, wherein the one or more dead volumes include a first dead volume and a second dead volume in series along the sample line between the sample line inlet and the sample line outlet, wherein the one or more dead volumes provide a total dead volume.

Embodiment F: The focused sampling method of Embodiment E further comprising, subsequent the discontinuing the flow from the guard line into the common line, introducing the combined flow comprising the flow of fluid from the sample line to the discard line via the combined flow line for a flushing time period prior to the introducing the combined flow comprising the flow of fluid from the sample line into the one or more sample chambers, and wherein the flushing time period is a time sufficient to pass a volume of at least three times the total dead volume to the discard line.

Embodiment G: The focused sampling method of any of Embodiment A to Embodiment F, wherein allocating comprises selecting or adjusting a restrictor valve positioned on or upstream of the sample line, a restrictor valve positioned on or upstream of the guard line, or both.

Embodiment H: The focused sampling method of Embodiment G, wherein the restrictor valve is a variably controlled restrictor valve.

Embodiment I: The focused sampling method of any of Embodiment A to Embodiment H, wherein discontinuing the flow from the guard line into the common line comprises actuating a flow restrictor (e.g., variable or static) on the guard line.

Embodiment J: The focused sampling method of any of Embodiment A to Embodiment I further comprising determining an end of the pre-sampling time by data received from one or more fluid identification (ID) sensors positioned on the guard line, the sample line, the common line, or a combination thereof.

Embodiment K: The focused sampling method of any of Embodiment A to Embodiment J, wherein the flow of fluid from the guard zone is greater than the flow of fluid from the sample zone during the pumping, via the common line, of the combined flow of fluid from the formation through to the discard line for the pre-sampling time period.

Embodiment L: The focused sampling method of any Embodiment A to Embodiment K, wherein the maximum contamination level comprises a total of less than or equal to 10, 9, 8, 7, 6, 5, 4, 3, 2, or 1 weight percent of one or more contaminants, wherein the one or more contaminants comprise components of the flow allocated in the sample line that are not present in the virgin fluid and/or present in the flow allocated to the sample line at a level greater than a level thereof in the virgin fluid.

Embodiment M: A focused sampling system comprising: a sample line having a sample line inlet and a sample line outlet; a guard line having a guard line inlet and a guard line outlet; a common line having a common line inlet and a common line outlet, wherein the common line inlet is fluidly connected with the sample line outlet and the guard line outlet, and wherein the common line outlet is fluidly connected with a pump suction side inlet; the pump, wherein a discharge side outlet of the pump is fluidly connected with a discard line and a sampling line, wherein the sampling line is fluidly connected with one or more sample chambers; one or more fluid identification (ID) sensors positioned on the guard line, the sample line, the common line, or a combination thereof; and a flow restrictor operable to prevent flow of fluid from the guard line to the common line.

Embodiment N: The focused sampling system of Embodiment M further comprising a probe defining a sample zone fluidly connected with the sample line inlet of the sample line a guard zone fluidly connected with the guard line inlet of the guard line, or both a sample zone fluidly connected with the sample line inlet of the sample line and a guard zone fluidly connected with the guard line inlet of the guard line.

Embodiment O: The focused sampling system of Embodiment N, wherein the guard zone is positioned at least partially concentrically about the sample zone.

Embodiment P: The focused sampling system of Embodiment N or Embodiment O, wherein the sample zone and the guard zone are oval or circular in cross section.

Embodiment Q: The focused sampling system of Embodiment N, wherein the probe defines the sample zone in fluid communication with the sample line inlet of the sample line, and wherein the focused sampling system further comprises one or more packers defining a guard zone, wherein the guard zone comprises an annulus around the sample zone, and wherein the guard zone is in fluid communication with the guard line inlet of the guard line.

Embodiment R: The focused sampling system of Embodiment M further comprising one or more first packers defining a sample zone, wherein the sample zone is in fluid communication with the sample line inlet of the sample line, and one or more second packers defining a guard zone, wherein the guard zone comprises an annulus around the sample zone, and wherein the guard zone is in fluid communication with the guard line inlet of the guard line.

Embodiment S: The focused sampling system of any of Embodiment M to Embodiment R further comprising one or more dead volumes in fluid communication with the sample line.

Embodiment T: The focused sampling system of Embodiment S, wherein the one or more dead volumes include a first dead volume and a second dead volume in series along the sample line.

Embodiment U: The focused sampling system of any of Embodiment M to Embodiment T further comprising a restrictor valve positioned on or upstream of the sample line, a restrictor valve positioned on or upstream of the guard line, or both, wherein the restrictor valve is operable to allocate flow of fluid from a guard zone into the guard line and flow of fluid from a sample zone into the sample line, wherein the guard zone is positioned at least partially concentrically about the sample zone and wherein the guard zone and the sample zone are in fluid communication with a formation.

Embodiment V: The focused sampling system of any of Embodiment M to Embodiment U, wherein the guard line is configured for a higher fluid flow rate than the sample line.

Embodiment W: A focused sampling system comprising: a sample line having a sample line inlet and a sample line outlet and containing fluid from a sample zone of a formation passing through the sample line at a sample line fluid flow allocated from the formation into the sample line; a guard line having a guard line inlet and a guard line outlet and containing fluid from a guard zone of the formation passing through the guard line at a guard line fluid flow allocated from the formation into the guard line; a common line having a common line inlet and a common line outlet, wherein the common line inlet is fluidly connected with the sample line outlet and the guard line outlet and has a common line fluid flow comprising the guard line fluid flow allocated from the guard zone into the guard line and the sample line fluid flow allocated from the sample zone to the sample line, and wherein the common line outlet is fluidly connected with a pump suction side inlet; the pump, wherein a discharge side outlet of the pump is fluidly connected with a discard line and a sampling line, and wherein the sampling line is fluidly connected with one or more sample chambers; one or more fluid identification (ID) sensors positioned on the guard line, the sample line, the common line, or a combination thereof; and a flow restrictor operable to prevent flow of fluid from the guard line to the common line in a first configuration and allow flow of fluid from the guard line to the common line in a second configuration.

Embodiment X: The focused sampling system of Embodiment W, wherein the focused sampling system is in a pre-sampling mode, during which a purity of the fluid in the sample line, as determined by the one or more fluid ID sensors, is below the desired purity, wherein the flow restrictor is in the second configuration and thus allowing flow of fluid from the guard line to the common line, wherein the guard line fluid flow is greater than the sample line fluid flow, and wherein the pump is configured for pumping of fluid from the common line to the discard line.

Embodiment Y: The focused sampling system of Embodiment W, wherein the focused sampling system is in a sampling mode, initiated when a purity of the fluid in the sample line, as determined by the one or more fluid ID sensors, is at or above the desired purity, wherein the flow restrictor is in the first configuration and thus preventing flow of fluid from the guard line to the common line, and wherein the pump is configured for pumping of fluid from the common line to the one or more sample chambers.

Embodiment Z1: A focused sampling method comprising: positioning a sampling device adjacent a sampling zone of a wellbore within a formation, wherein the sampling device comprises: a sample line having a sample line inlet and a sample line outlet; a guard line having a guard line inlet and a guard line outlet; a common line having a common line inlet and a common line outlet, wherein the common line inlet is fluidly connected with the sample line outlet and the guard line outlet, and wherein the common line outlet is fluidly connected with a pump suction side inlet; the pump, wherein a discharge side outlet of the pump is fluidly connected with a discard line and a sampling line, wherein the sampling line is fluidly connected with one or more sample chambers; one or more fluid identification (ID) sensors positioned on the guard line, the sample line, the common line, or a combination thereof; and a flow restrictor configured to prevent flow of fluid from the guard line to the common line in a first configuration and allow flow of fluid from the guard line to the common line in the second configuration; pumping fluid from a sample zone of the formation into the common line via the sample line and from a guard zone of the formation into the common line via the guard line, and from the common line into the discard line for a pre-sampling period in which the flow restrictor is in the second configuration; monitoring a purity of the fluid in the sample line via the one or more fluid ID sensors; upon detecting that the purity of the fluid in the sample line is at or above a desired purity: discontinuing flow of fluid from the guard zone into the common line by configuring the flow restrictor in the first configuration; flushing the system by passing a flush volume of fluid from the sample zone of the formation to the discard line via the sample line and the common line; and filling the one or more sample chambers by pumping fluid from the common line into the one or more sample chambers.

Embodiment Z2: The focused sampling method of Embodiment Z1 further comprising: prior to positioning the sampling device adjacent the sampling zone of the wellbore within the formation, setting the flow restrictor or another flow restrictor of the sampling device to provide a desired flow volume ratio between the guard line and the sample line.

Embodiment Z3: The focused sampling method of Embodiment Z1 or Embodiment Z2, wherein the sampling device is a part of a wireline assembly or a bottom hole assembly (BHA).

Embodiment Z4: The focused sampling method of any of Embodiment Z1 to Embodiment Z3, wherein the flush volume is at least three times a volume of fluid contained by the sampling device between the sample line inlet and the sample line outlet.

Embodiment Z5: The focused sampling method of any of Embodiment Z1 to Embodiment Z4, wherein the sampling device further comprises one or more dead volumes fluidly connected with the sample line, and wherein filling the one or more sample chambers by pumping fluid from the common line into the one or more sample chambers comprises pumping fluid from the one or more dead volumes into the common line and from the common line into the one or more sample chambers.

Embodiment Z6: The focused sampling method of Embodiment Z5, wherein the one or more dead volumes are offline dead volumes, and wherein the method further comprises, upon detecting that the purity of the fluid in the sample line is at or above the desired purity, diverting flow of fluid from the sample inlet of the sample line to the one or more dead volumes.

Embodiment Z7: The focused sampling method of any of Embodiment Z1 to Embodiment Z6, wherein the sampling device comprises a fluid ID sensor on the sample line and a fluid ID sensor on the guard line, a fluid ID sensor on the common line, or both a fluid ID sensor on the guard line and a fluid ID sensor on the common line, and wherein monitoring the purity of the fluid in the sample line via the one or more fluid ID sensors further comprises comparing measurements obtained from the fluid ID sensor on the sample line with measurements obtained from the fluid ID sensor on the guard line and/or the fluid ID sensor on the common line.

Embodiment Z8: The focused sampling method of any of Embodiment Z1 to Embodiment Z7 further comprising: discontinuing drilling prior to positioning the sampling device adjacent the sampling zone; retrieving the one or more sample chambers from the wellbore; continuing drilling within the formation; or any combination or repetition of one or more thereof.

Embodiment Z9: A focused sampling method comprising: placing a formation fluid sampling device adjacent a sampling zone in a wellbore penetrating a subterranean formation; concurrently pumping, via a common pump disposed within the sampling device, a sample flow of formation fluid in a sample flow line from the subterranean formation into the sampling device and a guard flow of formation fluid in a guard flow line from the subterranean formation into the sampling device, wherein the guard flow rate is greater than the sample flow rate and forms a guard zone around and adjacent the sample zone within the sampling zone; during the concurrently pumping, analyzing the formation fluid in the sample flow line to determine whether an amount of contaminant within the formation fluid in the sample flow line has dropped below a threshold value; and upon determining that the amount of contaminant within the formation fluid in the sample flow line has dropped below a threshold value, decreasing or discontinuing the guard flow of the formation fluid in the guard flow line and diverting the sample flow of the formation fluid in the sample flow line to a sample chamber.

While embodiments have been shown and described, modifications thereof can be made by one skilled in the art without departing from the spirit and teachings of this disclosure. The embodiments described herein are exemplary only, and are not intended to be limiting. Many variations and modifications of the embodiments disclosed herein are possible and are within the scope of this disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, Rl, and an upper limit, Ru, is disclosed, any number falling within the range is specifically disclosed. In particular, the following numbers within the range are specifically disclosed: $R=Rl+k*(Ru-Rl)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the embodiments of the present disclosure. The discussion of a reference herein is not an admission that it is prior art, especially any reference that may have a publication date after the priority date of this application. The disclosures of all patents, patent applications, and publications cited herein are hereby incorporated by reference, to the extent that they provide exemplary, procedural, or other details supplementary to those set forth herein.

We claim:
1. A focused sampling method comprising:
allocating flow of fluid from a guard zone through a guard line and flow of fluid from a sample zone through a sample line, wherein the guard zone is positioned at least partially concentrically about the sample zone and wherein the guard zone and the sample zone are in fluid communication with a formation, wherein the sample line is in fluid communication with one or more dead volumes, wherein the one or more dead volumes provide a total dead volume, and wherein the one or more dead volumes comprise a first dead volume and a second dead volume in series along the sample line between a sample line inlet and a sample line outlet or wherein the one or more dead volumes include one or more offline dead volumes;

pumping, via a common line, a combined flow of fluid from the formation through to a discard line for a pre-sampling time period until the flow allocated into the sample line from the sample zone comprises formation fluid having a contamination level below a maximum contamination level, wherein the combined flow comprises the flow of fluid allocated from the guard zone into the guard line and the flow of fluid allocated from the sample zone into the sample line;

subsequent the pre-sampling time period, discontinuing flow from the guard line into the common line, such that the combined flow comprises only the flow of fluid from the sample line;

introducing the combined flow comprising the flow of fluid from the sample line into one or more sample chambers; and subsequent the discontinuing the flow from the guard line into the common line, introducing the combined flow comprising the flow of fluid from the sample line to the discard line via the combined flow line for a flushing time period prior to the introducing the combined flow comprising the flow of fluid from the sample line into the one or more sample chambers.

2. A focused sampling method comprising:

positioning a sampling device adjacent a sampling zone of a wellbore within a formation,
  wherein the sampling device comprises:
    a sample line having a sample line inlet and a sample line outlet, wherein the sample line is fluidly connected with one or more dead volumes, wherein the one or more dead volumes comprise a first dead volume and a second dead volume in series along the sample line between the sample line inlet and the sample line outlet;
    a guard line having a guard line inlet and a guard line outlet;
    a common line having a common line inlet and a common line outlet, wherein the common line inlet is fluidly connected with the sample line outlet and the guard line outlet, and wherein the common line outlet is fluidly connected with a pump having a pump suction side inlet;
    the pump, wherein a discharge side outlet of the pump is fluidly connected with a discard line and a sampling line, wherein the sampling line is fluidly connected with one or more sample chambers;
    one or more fluid identification (ID) sensors positioned on the guard line, the sample line, the common line, or a combination thereof; and
    a flow restrictor configured to prevent flow of fluid from the guard line to the common line in a first configuration and allow flow of fluid from the guard line to the common line in the second configuration;

pumping fluid from a sample zone of the formation into the common line via the sample line and from a guard zone of the formation into the common line via the guard line, and from the common line into the discard line for a pre-sampling period in which the flow restrictor is in the second configuration;

monitoring a purity of the fluid in the sample line via the one or more fluid ID sensors;

upon detecting that the purity of the fluid in the sample line is at or above a desired purity:
  discontinuing flow of fluid from the guard zone into the common line by configuring the flow restrictor in the first configuration;
  flushing the system by passing a flush volume of fluid from the sample zone of the formation to the discard line via the sample line and the common line; and
  filling the one or more sample chambers by pumping fluid from the common line into the one or more sample chambers.

3. The focused sampling method of claim 1, wherein a sample line volume is greater than a guard line volume, wherein the sample line volume is a volume from the sample line inlet to the sample line outlet, and wherein the guard line volume is a volume from the guard line inlet to the guard line outlet.

4. The focused sampling method of claim 3, wherein the flushing time period is a time sufficient to pass a volume of at least three times the total dead volume to the discard line.

5. The focused sampling method of claim 1, wherein allocating comprises selecting or adjusting a restrictor valve positioned on or upstream of the sample line, a restrictor valve positioned on or upstream of the guard line, or both.

6. The focused sampling method of claim 1, wherein discontinuing the flow from the guard line into the common line comprises actuating a flow restrictor on the guard line.

7. The focused sampling method of claim 1 further comprising determining an end of the pre-sampling time by data received from one or more fluid identification (ID) sensors positioned on the guard line, the sample line, the common line, or a combination thereof.

8. The focused sampling method of claim 1, wherein the flow of fluid from the guard zone is greater than the flow of fluid from the sample zone during the pumping, via the common line, of the combined flow of fluid from the formation through to the discard line for the pre-sampling time period.

9. A focused sampling system comprising:
  a sample line having a sample line inlet and a sample line outlet,
    wherein the sample line is in fluid communication with one or more dead volumes, and
    wherein the one or more dead volumes include a first dead volume and a second dead volume in series along the sample line between a sample line inlet and a sample line outlet or wherein the one or more dead volumes include one or more offline dead volumes;
  a guard line having a guard line inlet and a guard line outlet;
  a common line having a common line inlet and a common line outlet, wherein the common line inlet is fluidly connected with the sample line outlet and the guard line outlet, and wherein the common line outlet is fluidly connected with a pump suction side inlet;
  the pump, wherein a discharge side outlet of the pump is fluidly connected with a discard line and a sampling line, wherein the sampling line is fluidly connected with one or more sample chambers;
  one or more fluid identification (ID) sensors positioned on the guard line, the sample line, the common line, or a combination thereof; and a flow restrictor operable to prevent flow of fluid from the guard line to the common line.

10. The focused sampling system of claim 9 further comprising a probe defining a sample zone fluidly connected with the sample line inlet of the sample line a guard zone fluidly connected with the guard line inlet of the guard line, or both a sample zone fluidly connected with the sample line inlet of the sample line and a guard zone fluidly connected with the guard line inlet of the guard line.

11. The focused sampling system of claim 10, wherein the guard zone is positioned at least partially concentrically about the sample zone.

12. The focused sampling system of claim 10, wherein the probe defines the sample zone in fluid communication with the sample line inlet of the sample line, and wherein the focused sampling system further comprises one or more packers defining a guard zone, wherein the guard zone comprises an annulus around the sample zone, and wherein the guard zone is in fluid communication with the guard line inlet of the guard line.

13. The focused sampling system of claim 9 further comprising one or more first packers defining a sample zone, wherein the sample zone is in fluid communication with the sample line inlet of the sample line, and one or more second packers defining a guard zone, wherein the guard zone comprises an annulus around the sample zone, and wherein the guard zone is in fluid communication with the guard line inlet of the guard line.

14. The focused sampling system of claim 9 wherein the one or more dead volumes in fluid communication with the sample line comprise the one or more offline dead volumes.

15. The focused sampling system of claim 9 further comprising a restrictor valve positioned on or upstream of the sample line, a restrictor valve positioned on or upstream of the guard line, or both, wherein the restrictor valve is operable to allocate flow of fluid from a guard zone into the guard line and flow of fluid from a sample zone into the sample line, wherein the guard zone is positioned at least partially concentrically about the sample zone and wherein the guard zone and the sample zone are in fluid communication with a formation.

16. The focused sampling method of claim 2 further comprising, subsequent the discontinuing the flow of fluid from the guard zone into the common line by configuring the flow restrictor in the first configuration, introducing the combined flow comprising the flow of fluid from the sample line to the discard line via the combined flow line for a flushing time period prior to the introducing the combined flow comprising the flow of fluid from the sample line into the one or more sample chambers.

17. The focused sampling method of claim 2 further comprising:
prior to positioning the sampling device adjacent the sampling zone of the wellbore within the formation, setting the flow restrictor or another flow restrictor of the sampling device to provide a desired flow volume ratio between the guard line and the sample line.

18. The focused sampling method of claim 2, wherein filling the one or more sample chambers by pumping fluid from the common line into the one or more sample chambers comprises pumping fluid from the one or more dead volumes into the common line and from the common line into the one or more sample chambers.

19. The focused sampling method of claim 2 further comprising:
discontinuing drilling prior to positioning the sampling device adjacent the sampling zone;
retrieving the one or more sample chambers from the wellbore;
continuing drilling within the formation; or
any combination or repetition of one or more thereof.

20. A focused sampling method comprising:
positioning a sampling device adjacent a sampling zone of a wellbore within a formation,
wherein the sampling device comprises:
a sample line having a sample line inlet and a sample line outlet;
a guard line having a guard line inlet and a guard line outlet;
a common line having a common line inlet and a common line outlet, wherein the common line inlet is fluidly connected with the sample line outlet and the guard line outlet, and wherein the common line outlet is fluidly connected with a pump suction side inlet;
the pump, wherein a discharge side outlet of the pump is fluidly connected with a discard line and a sampling line, wherein the sampling line is fluidly connected with one or more sample chambers;
one or more fluid identification (ID) sensors positioned on the guard line, the sample line, the common line, or a combination thereof; and
a flow restrictor configured to prevent flow of fluid from the guard line to the common line in a first configuration and allow flow of fluid from the guard line to the common line in the second configuration;
pumping fluid from a sample zone of the formation into the common line via the sample line and from a guard zone of the formation into the common line via the guard line, and from the common line into the discard line for a pre-sampling period in which the flow restrictor is in the second configuration;
monitoring a purity of the fluid in the sample line via the one or more fluid ID sensors;
upon detecting that the purity of the fluid in the sample line is at or above a desired purity:
discontinuing flow of fluid from the guard zone into the common line by configuring the flow restrictor in the first configuration;
flushing the system by passing a flush volume of fluid from the sample zone of the formation to the discard line via the sample line and the common line; and
filling the one or more sample chambers by pumping fluid from the common line into the one or more sample chambers,
wherein the one or more dead volumes are offline dead volumes, and wherein the method further comprises, upon detecting that the purity of the fluid in the sample line is at or above the desired purity, diverting flow of fluid from the sample inlet of the sample line to the one or more dead volumes.

* * * * *

UNITED STATES PATENT AND TRADEMARK OFFICE
CERTIFICATE OF CORRECTION

PATENT NO. : 11,125,083 B2
APPLICATION NO. : 16/670886
DATED : September 21, 2021
INVENTOR(S) : Christopher Michael Jones et al.

Page 1 of 1

It is certified that error appears in the above-identified patent and that said Letters Patent is hereby corrected as shown below:

In the Specification

-Column 9, Line 27, replace "1010B" with -- 10B --.

-Column 9, Line 56, replace "853" with -- 85B --.

-Column 10, Line 17, replace "853" with -- 85B --.

Signed and Sealed this
Twenty-sixth Day of October, 2021

Drew Hirshfeld
*Performing the Functions and Duties of the*
*Under Secretary of Commerce for Intellectual Property and*
*Director of the United States Patent and Trademark Office*